United States Patent
Yamamoto et al.

(10) Patent No.: US 6,951,843 B2
(45) Date of Patent: Oct. 4, 2005

(54) PEPTIDE DERIVATIVES AND THEIR PHARMACEUTICALLY ACCEPTABLE SALTS, THEREOF, PROCESSES FOR PREPARATION OF BOTH AND USE THEREOF

(75) Inventors: Kenji Yamamoto, Fukuoka (JP); Yoshimitsu Suda, Tokorozawa (JP); Tetsuji Asao, Kokubunji (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 469 days.

(21) Appl. No.: 10/168,540

(22) PCT Filed: Nov. 2, 2001

(86) PCT No.: PCT/JP01/09621

§ 371 (c)(1),
(2), (4) Date: Jul. 2, 2002

(87) PCT Pub. No.: WO02/36551

PCT Pub. Date: May 10, 2002

(65) Prior Publication Data

US 2003/0087828 A1 May 8, 2003

(30) Foreign Application Priority Data

Nov. 6, 2000 (JP) .......................... 2000-338192

(51) Int. Cl.$^7$ ............................................. A61K 38/00
(52) U.S. Cl. ...................................................... 514/16
(58) Field of Search ................................... 514/16

(56) References Cited

U.S. PATENT DOCUMENTS

| | | | | |
|---|---|---|---|---|
| 5,496,927 A | | 3/1996 | Kolb et al. | 530/328 |
| 5,849,866 A | | 12/1998 | Kolb et al. | 530/323 |
| 6,066,622 A | * | 5/2000 | Green et al. | 514/17 |
| 6,100,380 A | * | 8/2000 | Green et al. | 530/328 |
| 6,130,315 A | | 10/2000 | Kolb et al. | 530/328 |
| 6,346,514 B1 | * | 2/2002 | Green et al. | 514/17 |
| 2002/0071843 A1 | * | 6/2002 | Li et al. | 424/155.1 |

FOREIGN PATENT DOCUMENTS

| | | |
|---|---|---|
| JP | 5-97708 | 4/1993 |
| JP | 2529825 | 6/1996 |
| JP | 11-228526 | 8/1999 |

OTHER PUBLICATIONS

Abe et al. Design and synthesis of sensitive fluorogenic substrates specific for Lys–gingipain. J Biochem (Tokyo), Nov. 2000; 128(5): 877–81.*

The Tissue Culture Engineering, vol. 27(9) (Aug. 25, 2001); pp. 17–21; Partial Translation.

Robert Pike et al; "Lysine– and Arginine–specific Proteinases from *Porphyromonas gingivalis*"; J. Bio. Chem.; vol. 269 (1994); pp. 406–411.

Greiner et al; Biology of the Species *Porphyromonas gingivalis*; Chapter 13; CRC Press (1993); pp. 227–243.

Slots et al; "*Bacteroides gingivalis*, Bacteroides intermedius and Actinobacillus actino–mycetemcomitans in human periodontal diseases"; J. Clin. Periodontal 1988: 15; pp. 85–93.

Dzink et al; "The predominant cultivable microbiota of active and inactive lesions of destructive periodontal diseases"; J. Clin Periodontal 1988: 15; pp. 216–323.

Genco et al; "Host responses in Periodontal Diseases"; J. Dent Res. 63(3); (Mar. 1984); pp. 441–451.

International Search Report dated Jan. 22, 2002.

* cited by examiner

*Primary Examiner*—Christopher R. Tate
*Assistant Examiner*—Maury Audet
(74) *Attorney, Agent, or Firm*—Armstrong, Kratz, Quintos, Hanson & Brooks, LLP

(57) ABSTRACT

The present invention provides a peptide derivative of formula (I)

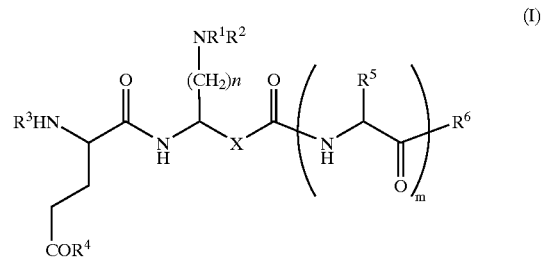

wherein X is —CHOH— or —CO—; $R^1$ and $R^2$ are hydrogen or substituted oxycarbonyl; $R^3$ is substituted oxycarbonyl; $R^4$ is hydroxyl, lower alkoxy, optionally substituted piperazinyl or the like; $R^5$ is a R-group side chain of an α-amino acid optionally protected by a protective group, $R^6$ is hydroxyl, lower alkoxy or the like; m is 0 or 1; and n is an integer of 2 to 6; or
a pharmaceutically acceptable salt thereof.

The present invention further provides a production process and use thereof.

12 Claims, No Drawings

PEPTIDE DERIVATIVES AND THEIR PHARMACEUTICALLY ACCEPTABLE SALTS, THEREOF, PROCESSES FOR PREPARATION OF BOTH AND USE THEREOF

TECHNICAL FIELD

The present invention relates to a novel peptide derivative and pharmaceutically acceptable salts thereof, and a production process and use thereof.

BACKGROUND ART

Most periodontal diseases are considered to be a kind of infectious disease caused by indigenous microbes residing in the periodontal area. It has been revealed that a gram-negative anaerobic bacterium called *Porphyromonas gingivalis* (hereinafter abbreviated as "*P. gingivalis*") is the most important pathogenic bacterium in the infections that cause adult periodontitis and rapidly progressive periodontitis (J. Clin. Periodontol., 15, 85–93, 1988, ibid 316–323, 1988; J. Dent. Res., 63, 441–451, 1984). In recent years, it has become known that proteases produced by *P. gingivalis* decompose periodontal tissue components such as collagen, and blood serum proteins involved in the body's natural defense system and are intimately related to the pathogenicity of *P. gingivalis* (Greiner D.: Biology of the Species *Porphyromonas Gingivalis*, Edited by Shah H. N., Mayrrand D. and Genco R. J., pp.227–243, CRC Press, Boca Raton, Ann Arbor, London, Tokyo, 1993). For example, Lys-gingipain (hereinafter sometimes abbreviated as "KGP"), a proteolytic enzyme having trypsin-like protease activity and produced by *P. gingivalis*, is known to have a high ability to digest high molecular weight kininogen and fibrinogen and considered to play a role in the onset of periodontal disease and destruction of periodontal tissues (J. Biol. Chem., 269, 406–411, 1994).

In order to prevent and treat periodontal disease, drugs for inhibiting the growth of bacteria are conventionally used. Useful drugs include, for example, antibiotics such as tetracycline and minocycline; natural products such as chamomile tincture and rhatany tincture; cyclohexadine, tranexamic acid and the like. However, these drugs have safety problems or other various problems such as unpleasant smell. Japanese Unexamined Patent Publication No. 97708/1993 discloses a periodontal therapeutic agent comprising an ATPase inhibitor, a cysteine protease inhibitor or the like as an active ingredient. However, the anti-periodontal disease effect of this therapeutic agent is unsatisfactory.

Japanese Patent No. 2529825 describes various peptidase substrate analogues but nowhere mentions peptide derivatives having a glutamic acid-lysine derivative structure as the basic skeleton, like the compound of the present invention. In addition, there is no description about compounds having KGP-specific inhibitory effects or compounds useful for treating periodontal diseases.

DISCLOSURE OF THE INVENTION

An object of the invention is to provide a novel compound which has the ability to potently and selectively inhibit Lys-gingipain and a production process thereof.

Another object of the invention is to provide a novel Lys-gingipain inhibitor and a pharmaceutical preparation for periodontal disease.

A further object of the invention is to provide a novel composition for use in the oral cavity.

A still further object of the invention is to provide a novel method for preventing or treating periodontal disease.

Other objects and features of the invention will become apparent from the following description.

The present invention provides the following peptide derivatives and pharmaceutically acceptable salts thereof, production processes and uses thereof.

1. A peptide derivative of formula (I)

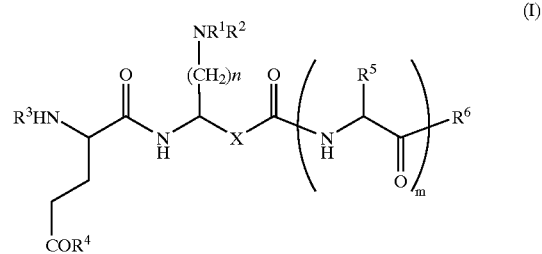

wherein X is —CHOH— or —CO—; $R^1$ and $R^2$ may be the same or different and are hydrogen or substituted oxycarbonyl; $R^3$ is substituted oxycarbonyl; $R^4$ is hydroxyl, lower alkoxy, optionally substituted piperazinyl, or —$NR^7R^8$ (wherein $R^7$ and $R^8$ may be the same or different and are hydrogen, optionally substituted lower alkyl, or amino optionally substituted with lower alkyl(s) or aryl(s)); $R^5$ is a R-group side chain of an α-amino acid optionally protected by a protective group; $R^6$ is hydroxyl, lower alkoxy, or —$NR^9R^{10}$ (wherein $R^9$ and $R^{10}$ may be the same or different and are hydrogen, lower alkyl, aryl or aralkyl); m is 0 or 1; and n is an integer of 2 to 6; or a pharmaceutically acceptable salt thereof.

2. The peptide derivative according to item 1 wherein n is 4; or a pharmaceutically acceptable salt thereof.

3. The peptide derivative according to item 1 wherein X is —CO—; or a pharmaceutically acceptable salt thereof.

4. The peptide derivative according to item 1 wherein $R^1$ and $R^2$ may be the same or different and are hydrogen or lower alkyloxycarbonyl and $R^3$ is optionally substituted aralkyloxycarbonyl; or a pharmaceutically acceptable salt thereof.

5. The peptide derivative according to item 4 wherein $R^4$ is hydroxyl, lower alkoxy, piperazinyl optionally having lower alkyl as a substituent, or —$NR^7R^8$ (wherein $R^7$ and $R^8$ may be the same or different and are hydrogen, lower alkyl optionally having amino or lower alkoxycarbonylamino as a substituent, or amino optionally substituted with lower alkyl(s) or phenyl(s)); $R^6$ is hydroxyl, lower alkoxy or —$NR^9R^{10}$ (wherein $R^9$ and $R^{10}$ may be the same or different and are hydrogen, lower alkyl, phenyl, benzyl or phenethyl); and n is 4; or a pharmaceutically acceptable salt thereof.

6. The peptide derivative according to item 5 wherein m is 0 and $R^6$ is hydroxyl or —$NR^9R^{10}$ (wherein $R^9$ and $R^{10}$ may be the same or different and are lower alkyl or phenethyl, or one of $R^9$ and $R^{10}$ is hydrogen and the other is phenethyl); or a pharmaceutically acceptable salt thereof.

7. The peptide derivative according to item 5 wherein m is 1, $R^5$ is isobutyl, carbamoylmethyl optionally protected by a protective group, 2-carboxyethyl optionally protected by a protective group, 4-aminobutyl optionally protected by a protective group, or benzyl, and $R^6$ is —$NR^9R^{10}$ (wherein $R^9$ and $R^{10}$ may be the same or different and are lower alkyl); or a pharmaceutically acceptable salt thereof.

8. The peptide derivative according to item 1 wherein X is —CO—, $R^1$ and $R^2$ are hydrogen, $R^3$ is benzyloxycarbonyl, $R^4$ is hydroxyl, $R^5$ is isobutyl, carbamoylmethyl, 2-carboxyethyl, 4-aminobutyl or benzyl, $R^6$ is —$NR^9R^{10}$ (wherein $R^9$ and $R^{10}$ are methyl), m is 1, and n is 4; or a pharmaceutically acceptable salt thereof.

9. The peptide derivative according to item 1 wherein X is —CO—, $R^1$ and $R^2$ are hydrogen, $R^3$ is benzyloxycarbonyl, $R^4$ is hydroxyl, amino, methylamino, dimethylamino, (2-aminoethyl)amino, piperazinyl, 1,1-dimethylhydrazino or 1-methyl-1-phenylhydrazino, $R^6$ is n-propylamino, phenylamino, benzylamino or phenethylamino, m is 0, and n is 4; or a pharmaceutically acceptable salt thereof.

10. A process for preparing a peptide derivative of formula (I)

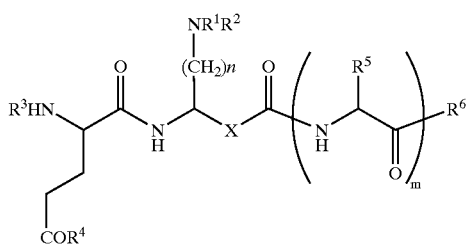
(I)

wherein X is —CHOH— or —CO—; $R^1$ and $R^2$ may be the same or different and are hydrogen or substituted oxycarbonyl; $R^3$ is substituted oxycarbonyl; $R^4$ is hydroxyl, lower alkoxy, optionally substituted piperazinyl, or —$NR^7R^8$ (wherein $R^7$ and $R^8$ may be the same or different and are hydrogen, optionally substituted lower alkyl, or amino optionally substituted with lower alkyl(s) or aryl(s)); $R^5$ is a R-group side chain of an α-amino acid optionally protected by a protective group; $R^6$ is hydroxyl, lower alkoxy, or —$NR^9R^{10}$ (wherein $R^9$ and $R^{10}$ may be the same or different and are hydrogen, lower alkyl, aryl or aralkyl); m is 0 or 1; and n is an integer of 2 to 6, or a pharmaceutically acceptable salt thereof, the process comprising the following step (i): (i) carrying out a condensation reaction between a compound of formula (II)

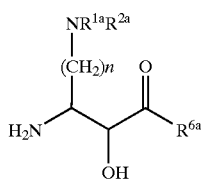
(II)

wherein n is as defined above, $R^{1a}$ is hydrogen or substituted oxycarbonyl, $R^{2a}$ is substituted oxycarbonyl, and $R^{6a}$ is lower alkoxy, and
a compound of formula (III)

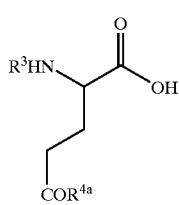
(III)

wherein $R^3$ is as defined above and $R^{4a}$ is hydroxyl or lower alkoxy to produce a peptide derivative of formula (I-a)

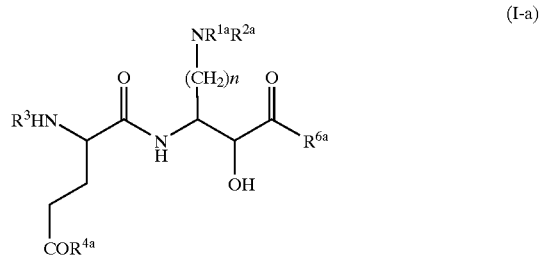
(I-a)

wherein $R^{1a}$, $R^{2a}$, $R^3$, $R^{4a}$, $R^{6a}$ and n are as defined above, or a pharmaceutically acceptable salt thereof.

11. A process for preparing a peptide derivative of formula (I) or a pharmaceutically acceptable salt thereof, comprising the following step (ii): (ii) hydrolyzing a compound of formula (I-a) with a base to produce a peptide derivative of formula (I-b)

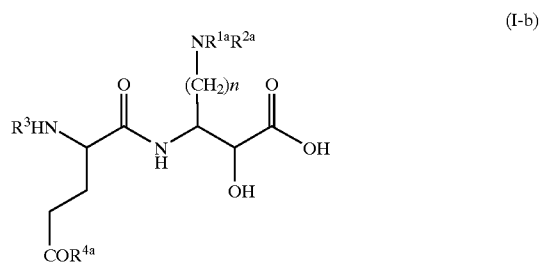
(I-b)

wherein $R^{1a}$, $R^{2a}$, $R^3$, $R^{4a}$, $R^{6a}$ and n are as defined above, or a pharmaceutically acceptable salt thereof.

12. A process for preparing a peptide derivative of formula (I) or a pharmaceutically acceptable salt thereof, comprising the following step (iii): (iii) carrying out a condensation reaction between a compound of formula (I-b) and a compound of formula (IV)

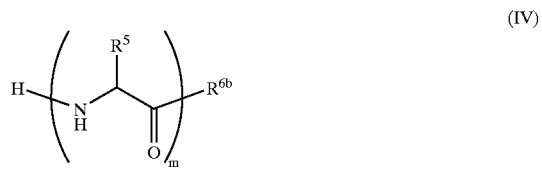
(IV)

wherein $R^5$ and m are as defined above and $R^{6b}$ is hydroxyl, lower alkoxy or —$NR^9R^{10}$ (wherein $R^9$ and $R^{10}$ are as defined above), with the proviso that when m is 0, $R^{6b}$ is not hydroxyl, to produce a peptide derivative of formula (I-c)

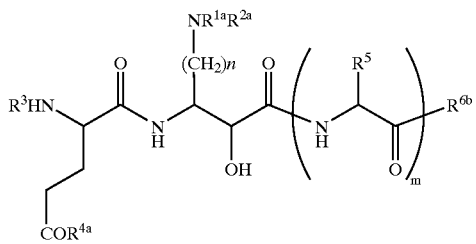
(I-c)

wherein $R^{1a}$, $R^{2a}$, $R^3$, $R^{4a}$, $R^5$, $R^{6b}$, m and n are as defined above, or a pharmaceutically acceptable salt thereof.

13. A process for preparing a peptide derivative of formula (I) or a pharmaceutically acceptable salt thereof, comprising the following step (iv): (iv) oxidizing a compound of formula (I-a), (I-b) or (I-c) to produce a peptide derivative of formula (I-d)

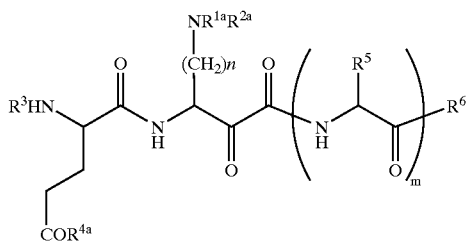
(I-d)

wherein $R^{1a}$, $R^{2a}$, $R^3$, $R^{4a}$, $R^5$, $R^6$, m and n are as defined above, or a pharmaceutically acceptable salt thereof.

14. A process for preparing a peptide derivative of formula (I) or a pharmaceutically acceptable salt thereof, comprising the following step (v): (v) treating a compound of formula (I-a), (I-b), (I-c) or (I-d) with an acid to produce a peptide derivative of formula (I-e)

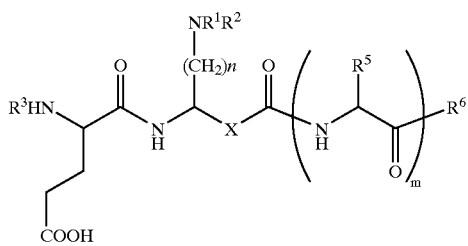
(I-e)

wherein X, $R^1$, $R^2$, $R^3$, $R^5$, $R^6$, m and n are as defined above, or a pharmaceutically acceptable salt thereof.

15. A process for preparing a peptide derivative of formula (I) or a pharmaceutically acceptable salt thereof, comprising the following step (vi): (vi) carrying out a condensation reaction of a compound of formula (I-f)

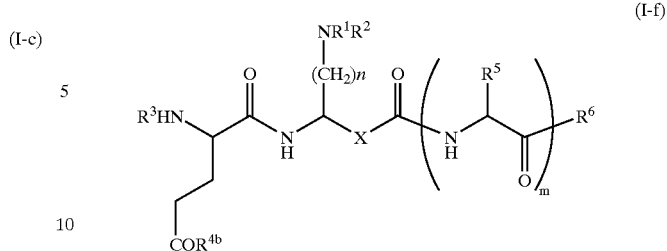
(I-f)

wherein X, $R^1$, $R^2$, $R^3$, $R^5$, $R^6$, m and n are as defined above and $R^{4b}$ is hydroxyl or lower alkoxy, with a lower alcohol, an optionally substituted piperazine or an amine represented by $NHR^7R^8$ (wherein $R^7$ and $R^8$ are as defined above) to produce a peptide derivative of formula (I.g)

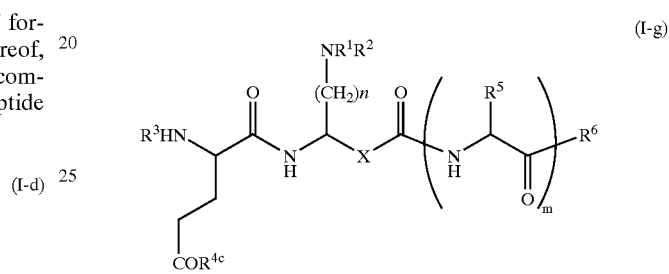
(I-g)

wherein X, $R^1$, $R^2$, $R^3$, $R^5$, $R^6$, m and n are as defined above, $R^{4c}$ is lower alkoxy, optionally substituted piperazinyl, or $-NR^7R^8$ (wherein $R^7$ and $R^8$ are as defined above), or a pharmaceutically acceptable salt thereof.

16. A process for preparing a peptide derivative of formula (I) or a pharmaceutically acceptable salt thereof, comprising the following step (vii): (vii) protecting an amino group of a compound of formula (I-h)

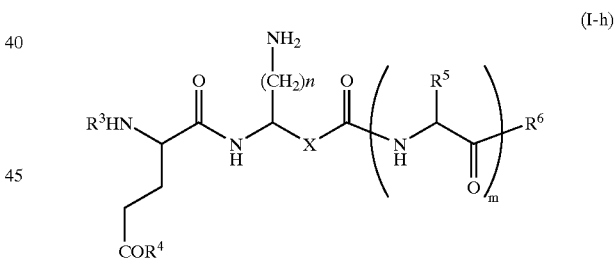
(I-h)

wherein X, $R^3$, $R^4$, $R^5$, $R^6$, m and n are as defined above using a substituted oxycarbonyl-introducing reagent to produce a peptide derivative of formula (I-i)

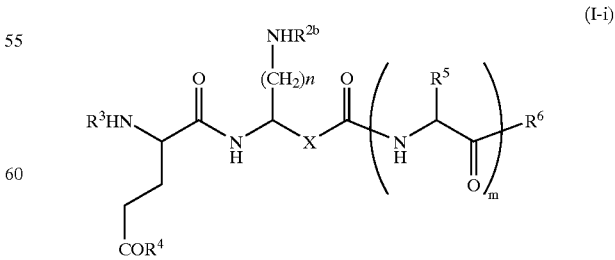
(I-i)

wherein X, $R^3$, $R^4$, $R^5$, $R^6$, m and n are as defined above and $R^{2b}$ is substituted oxycarbonyl, or a pharmaceutically acceptable salt thereof.

17. A Lys-gingipain inhibitor comprising the peptide derivative of formula (I) of item 1 or a pharmaceutically acceptable salt thereof as an active ingredient.

18. A pharmaceutical preparation for periodontal disease comprising the peptide derivative of formula (I) of item 1 or a pharmaceutically acceptable salt thereof as an active ingredient.

19. A composition for use in the oral cavity comprising the peptide derivative of formula (I) of item 1 or a pharmaceutically acceptable salt thereof and a pharmaceutically acceptable carrier.

20. A method of preventing periodontal disease, comprising administering an effective amount of the Lys-gingipain inhibitor of item 17 to mammals, including humans.

21. A method of preventing periodontal disease, comprising administering an effective amount of the pharmaceutical preparation for periodontal disease of item 18 to mammals, including humans.

22. A method of preventing periodontal disease, comprising administering an effective amount of the composition for oral cavity of item 19 to mammals, including humans.

23. A method of treating periodontal disease, comprising administering an effective amount of the Lys-gingipain inhibitor of item 17 to mammals with periodontal disease, including humans.

24. A method of treating periodontal disease, comprising administering an effective amount of the pharmaceutical preparation for periodontal disease of item 18 to mammals with periodontal disease, including humans.

25. A method of treating periodontal disease, comprising administering an effective amount of the composition for use in the oral cavity of item 19 to mammals with periodontal disease, including humans.

26. Use of the peptide derivative of item 1 or a pharmaceutically acceptable salt thereof for preparing the Lys-gingipain inhibitor of item 17.

27. Use of the peptide derivative of item 1 or a pharmaceutically acceptable salt thereof for preparing the pharmaceutical preparation for periodontal disease of item 18.

28. Use of the peptide derivative of item 1 or a pharmaceutically acceptable salt thereof for preparing the composition for oral cavity of item 19.

The present inventors focused on the fact that *P. gingivalis* plays a significant role in the onset and progress of periodontal disease and that KGP, a proteolytic enzyme produced by *P. gingivalis*, causes periodontal disease. The inventors carried out intensive research to produce an effective preventive and therapeutic agent for periodontal disease. As a result, the inventors found that a novel peptide derivative capable of potently and selectively inhibiting KGP is highly effective as a periodontal preventive and therapeutic agent. The inventors further carried out a variety of research based on this finding and accomplished the present invention.

In formula (I), the substituted oxycarbonyl group represented by $R^1$, $R^2$ or $R^3$ is not specifically limited as long as it does not affect living organisms or synthetic reactions, and suitable examples thereof are commonly used amino protective groups. Examples thereof include optionally substituted aralkyloxycarbonyl, optionally substituted lower alkyloxycarbonyl, 1-adamantyloxycarbonyl and cyclopentyloxycarbonyl.

Examples of optionally substituted aralkyloxycarbonyl groups include benzyloxycarbonyl (abbreviated as Cbz); benzyloxycarbonyl substituted with 1 or 2 $C_{1-4}$ lower alkoxy groups, such as p-methoxybenzyloxycarbonyl and p-ethoxybenzyloxycarbonyl; benzyloxycarbonyl substituted with 1 or 2 nitro groups, such as p-nitrobenzyloxycarbonyl; benzyloxycarbonyl substituted with 1 or 2 halogen atoms, such as p-bromobenzyloxycarbonyl and 2,4-dichlorobenzyloxycarbonyl; and diphenylmethoxycarbonyl and the like. Particularly preferred is, for example, benzyloxycarbonyl.

Examples of optionally substituted lower alkyloxycarbonyl groups include $C_{2-7}$ straight-chain or branched-chain lower alkyloxycarbonyl optionally substituted with 1 to 3 halogen atoms, such as methoxycarbonyl, ethoxycarbonyl, t-butoxycarbonyl (abbreviated as Boc), 9-fluorenylmethyloxycarbonyl and 2,2,2-trichloroethyloxycarbonyl. Particularly preferred is, for example, t-butoxycarbonyl.

Preferred examples of the substituted oxycarbonyl group represented by $R^1$ or $R^2$ are lower alkyloxycarbonyl optionally substituted with 1 to 3 halogen atoms, more preferably lower alkyloxycarbonyl, particularly preferably t-butoxycarbonyl (Boc).

Preferred examples of the substituted oxycarbonyl group represented by $R^3$ are optionally substituted aralkyloxycarbonyl, more preferably benzyloxycarbonyl optionally having 1 or 2 substituents selected from the group consisting of lower alkoxy, nitro and halogen, particularly preferably benzyloxycarbonyl (Cbz).

Examples of the lower alkoxy group represented by $R^4$ include $C_{1-6}$ straight-chain or branched-chain lower alkoxy such as methoxy, ethoxy, n-propoxy, isopropoxy, n-butoxy, isobutoxy, t-butoxy, n-pentyloxy, isopentyloxy, n-hexyloxy and isohexyloxy, preferably t-butoxy.

Examples of the optionally substituted piperazinyl group represented by $R^4$ include piperazinyl; piperazinyl substituted with $C_{1-4}$ straight-chain or branched-chain lower alkyl, such as N-methylpiperazinyl, N-ethylpiperazinyl and N-t-butylpiperazinyl; piperazinyl substituted with $C_{2-5}$ straight-chain or branched-chain lower alkoxycarbonyl, such as N-methoxycarbonylpiperazinyl, N-ethoxycarbonylpiperazinyl and N-t-butoxycarbonylpiperazinyl; N-benzyloxycarbonylpiperazinyl and the like. Preferred is piperazinyl optionally substituted with lower alkyl. More preferred are piperazinyl and N-t-butoxycarbonylpiperazinyl.

Examples of the optionally substituted lower alkyl group represented by $R^7$ or $R^8$ are $C_{1-6}$ straight-chain or branched-chain lower alkyl groups optionally having amino or $C_{2-5}$ lower alkoxycarbonylamino as a substituent. Specific examples include methyl, ethyl, n-propyl, isopropyl, n-butyl, isobutyl, t-butyl, hexyl, aminoethyl, aminopropyl, aminobutyl, methoxycarbonylaminomethyl, ethoxycarbonylaminoethyl and t-butoxycarbonylaminoethyl. Preferred are $C_{1-6}$ straight-chain or branched-chain lower alkyl groups optionally having amino or t-butoxycarbonylamino as a substituent. More preferred are methyl, ethyl, aminoethyl and t-butoxycarbonylaminoethyl.

Examples of the amino group optionally substituted with lower alkyl(s) or aryl(s) represented by $R^7$ or $R^8$ include amino; methylamino, dimethylamino, ethylamino, diethylamino, n-propylamino, isopropylamino, n-butylamino and isobutylamino and like amino having 1 or 2 $C_{1-4}$ straight-chain or branched-chain lower alkyl groups; phenylamino, N-methyl-N-phenylamino, N-ethyl-N-phenylamino, N,N-diphenylamino, naphthylamino and the like. Preferred is amino optionally substituted with lower alkyl(s) or phenyl(s). More preferred are amino, methylamino, dimethylamino, phenylamino and N-methyl-N-phenylamino.

The R-group side chain of the "R-group side chain of an α-amino acid optionally protected by a protective group" represented by $R^5$ is a characteristic side chain or residue attached to the α-carbon atom of an α-amino acid. For example, the R-group side chain for glycine is hydrogen; for alanine it is methyl; and for valine it is isopropyl. In this invention, the α-amino acid R-group side chain can be any known naturally occuring α-amino acid R-group side chain. Such side chains include, for example, hydrogen (for glycine), methyl (for alanine), isopropyl (for valine), n-butyl (norleucine), isobutyl (for leucine), 1-methylpropyl (for isoleucine), hydroxymethyl (for serine), 1-hydroxyethyl (for threonine), mercaptomethyl (for cysteine), 2-methylthioethyl (for methionine), carbamoylmethyl (for asparagine), carboxymethyl (for aspartic acid), 2-carboxyethyl (for glutamic acid), 2-carbamoylethyl (for glutamine), 4-aminobutyl (for lysine), benzyl (for phenylalanine) and 4-hydroxybenzyl (for thyrosin). Preferred are isobutyl, carbamoylmethyl, 2-carboxyethyl, 4-aminobutyl and benzyl.

The protective group of the "R-group side chain of an α-amino acid optionally protected by a protective group" is not particularly limited as long as it is a protective group known to protect the amino group on the above R-group side chain. Examples of useful protective groups are those described in T. W. Greene, "Protective groups in Organic Synthesis", A Wiley-Interscience Publication, John-Wiley & Sons, New York, 1981, pp.218–287. Specific examples include the above-mentioned substituted oxycarbonyl groups, preferably the above-mentioned optionally substituted lower alkyloxycarbonyl groups, more preferably $C_{2-7}$ straight-chain or branched-chain lower alkyloxycarbonyl groups, especially preferably t-butoxycarbonyl (Boc). The protective group for carboxyl on the above R-group side chain is not specifically limited as long as it is a conventional protective group known to form an ester or an ether with a carboxyl group. Examples include $C_{1-6}$ straight-chain or branched-chain substituted or unsubstituted lower alkyl groups such as methyl, ethyl, propyl, butyl, t-butyl, hexyl and trichloroethyl; substituted or unsubstituted aralkyl groups such as benzyl, p-nitrobenzyl, p-methoxybenzyl and diphenylmethyl; acyloxyalkyl groups such as acetoxymethyl, acetoxyethyl, propionyloxyethyl, pivaloyloxypropyl, benzoyloxymethyl, benzoyloxyethyl, benzylcarbonyloxymethyl and cyclohexylcarbonyloxymethyl; alkoxyalkyl groups such as methoxymethyl, ethoxyethyl and benzyloxymethyl; and other groups such as tetrahydropyranyl, dimethylaminoethyl, dimethylchlorosilyl and trichlorosilyl. Preferred are substituted or unsubstituted alkyl groups and substituted or unsubstituted aralkyl groups. More preferred are $C_{1-6}$ straight-chain or branched-chain substituted or unsubstituted lower alkyl groups. Particularly preferred is t-butyl.

Examples of the lower alkoxy group represented by $R^6$ are $C_{1-4}$ straight-chain or branched-chain alkoxy groups such as methoxy, ethoxy, n-propoxy, isopropoxy, n-butoxy, isobutoxy and t-butoxy. Preferred is methoxy.

Examples of the lower alkyl group represented by $R^9$ or $R^{10}$ are $C_{1-6}$ straight-chain or branched-chain lower alkyl groups such as methyl, ethyl, n-propyl, isopropyl, n-butyl, isobutyl, t-butyl and hexyl. Preferred are methyl, ethyl and n-propyl. Examples of the aryl group include phenyl, naphthyl and anthryl. Preferred is phenyl. Examples of the aralkyl group include benzyl and phenethyl.

Of the compounds of the invention, preferred are compounds of formula (I) wherein $R^1$ and $R^2$ may be the same or different and are hydrogen or lower alkyloxycarbonyl and $R^3$ is optionally substituted aralkyloxycarbonyl.

More preferred compounds of the invention are compounds of formula (1) wherein $R^4$ is hydroxyl, lower alkoxy, piperazinyl optionally substituted with lower alkyl or $-NR^7R^8$ (wherein $R^7$ and $R^8$ may be the same or different and are hydrogen, lower alkyl optionally substituted with amino or lower alkoxycarbonylamino, or amino optionally substituted with lower alkyl(s) or phenyl(s)); $R^6$ is hydroxyl, lower alkoxy or $-NR^9R^{10}$ (wherein $R^9$ and $R^{10}$ may be the same or different and are hydrogen, lower alkyl, phenyl, benzyl or phenethyl); and n is 4.

Of the compounds of the invention, when m is 0, preferred are those wherein $R^6$ is $-NR^9R^{10}$ (wherein $R^9$ and $R^{10}$ may be the same or different and are lower alkyl, or one of $R^9$ and $R^{10}$ is hydrogen and the other is phenethyl).

When m is 1, especially preferred compounds of the invention are those wherein $R^5$ is isobutyl, carbamoylmethyl optionally protected by a protective group, 2-carboxyethyl optionally protected by a protective group, 4-aminobutyl optionally protected by a protective group, or benzyl, and $R^6$ is $-NR^9R^{10}$ (wherein $R^9$ and $R^{10}$ may be the same or different and are lower alkyl).

Preferably, n is 4.

Preferably, X is $-CO-$.

Preferred examples of compounds of the invention are further described below.

(1) Compounds of formula (I) wherein X is $-CO-$, $R^1$ and $R^2$ are hydrogen, $R^3$ is benzyloxycarbonyl, $R^4$ is hydroxyl, $R^5$ is isobutyl, carbamoylmethyl, 2-carboxyethyl, 4-aminobutyl or benzyl, $R^6$ is $-NR^9R^{10}$ (wherein $R^9$ and $R^{10}$ are methyl), m is 1, and n is 4.

(2) Compounds of formula (I) wherein X is $-CO-$, $R^1$ and $R^2$ are hydrogen, $R^3$ is benzyloxycarbonyl, $R^4$ is hydroxyl, amino, methylamino, dimethylamino, (2-aminoethyl)amino, piperazinyl, 1,1-dimethylhydrazino or 1-methyl-1-phenylhydrazino, $R^6$ is n-propylamino, phenylamino, benzylamino or phenethylamino, m is 0, and n is 4.

There is no specific limitation on the pharmaceutically acceptable salts of the compounds of the invention. Examples thereof include pharmaceutically acceptable acid addition salts thereof. Useful acids include inorganic acid salts such as hydrochlorides and sulfates; and organic acid salts such as formates, trifluoroacetates, acetates, tartrates, maleates, fumarates, succinates and methanesulfonates. Preferred are hydrochlorides. The compounds of the invention or pharmaceutically acceptable salts thereof may be in the form of solvates such as hydrates.

The amino acid constituting the compound of the invention may be an L- or D-amino acid. Preferred is L-amino acid.

The compounds of the invention exist as enantiomers or diastereoisomers depending on the asymmetric carbon(s) in the molecular structure. These enantiomers and diastereoisomers are included in the scope of the invention. Such compounds can be used as an isomer mixture as they are or can be optically resolved by a usual method and used.

The compounds represented by formula (I) can be prepared according to the following reaction schemes.

Reaction Scheme 1

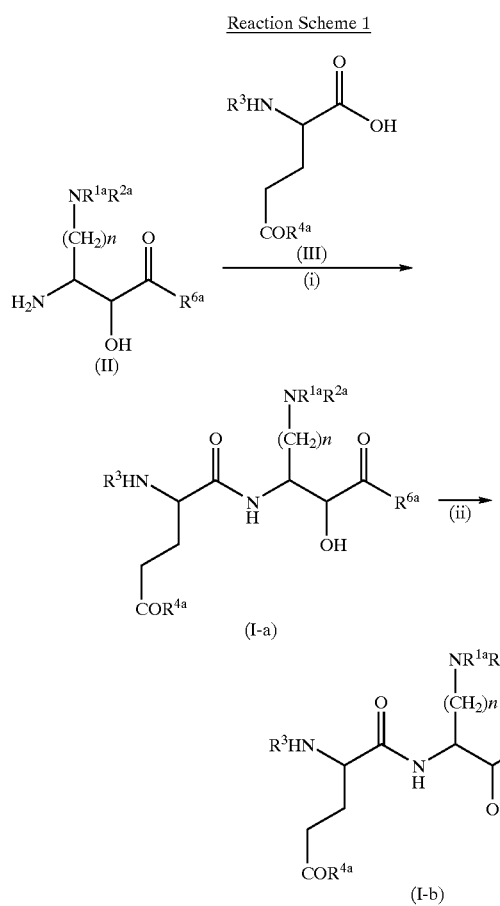

In the formulas, $R^3$ and n are as defined above; $R^{1a}$ is hydrogen or substituted oxycarbonyl; $R^{2a}$ is substituted oxycarbonyl; $R^{4a}$ is hydroxyl or lower alkoxy; and $R^{6a}$ is lower alkoxy.

Examples of the substituted oxycarbonyl group represented by $R^{1a}$ or $R^{2a}$ include those mentioned as examples of the substituted oxycarbonyl group represented by $R^1$ or $R^2$.

In view of the convenience of the reaction for synthesis, it is preferable that the substituted oxycarbonyl group represented by $R^{1a}$ or $R^{2a}$ be different from $R^3$. Examples of the lower alkoxy group represented by $R^{4a}$ include those mentioned as examples of the lower alkoxy group represented by $R^4$.

Examples of the lower alkoxy group represented by $R^{6a}$ include those mentioned as examples of the lower alkoxy group represented by $R^6$.

Step (i): A compound of formula (I-a) of the invention can be produced by a condensation reaction between a known compound of formula (II) (see, for example, WO98/50420) and a known compound of formula (III) in a suitable solvent.

The condensation reaction can be carried out by known methods. Useful methods include, for example, a method using a condensing agent such as N,N-dicyclohexylcarbodiimide and 1-ethyl-3-(3-dimethylaminopropyl)carbodiimide hydrochloride or a method using an additive (e.g., 1-hydroxybenzotriazole, N-hydroxy-5-norbornene-2,3-dicarboxyimide, etc.) in addition to the condensing agent; the mixed acid anhydride method using isobutyl chloroformate, etc.; the azide method; the active ester method; and the like. Any solvent that does not participate in this reaction can be used. Useful solvents include, for example, N,N-dimethylformamide, tetrahydrofuran, methylene chloride, dioxane, ethyl acetate, N-methylpyrrolidone, etc. These solvents can be used singly or in combinations of two or more. As to the amount each of the reagents, the amount of the compound of formula (III) is about 0.5 to 10 moles, preferably 1 to 5 moles, per mole of the compound of formula (II), and the amount of the condensing agent is about 0.5 to 10 moles, preferably 1 to 5 moles, per mole of the compound of formula (II), and the amount of the additive is about 0.5 to 10 moles, preferably 1 to 5 moles, per mole of the compound of formula (II). The reaction time is about 0.3 to 100 hours, preferably about 0.5 to 20 hours. The reaction temperature is about −10° C. to 100° C., preferably 0° C. to 40° C.

The compound obtained in this step can be used in the following reaction step, after being isolated or without isolation.

Step (ii): The compound of formula (I-b) of the invention is produced by hydrolysis of the compound of formula (I-a) with a suitable base, preferably in a suitable solvent. Examples of bases useful in this reaction include lithium hydroxide, sodium hydroxide and potassium hydroxide. The reaction temperature is about −20° C. to 50° C., preferably 0° C. to 40° C. Any solvent that does not participate in this reaction can be used. Useful solvents include, for example, water, methanol, ethanol, 1-propanol, 2-propanol, tetrahydrofuran, etc. These solvents can be used singly or in combinations of two or more. The amount of the reagent is about 0.5 to 10 moles, preferably 1 to 2 moles, per mole of the compound of formula (I-a). The reaction time is about 0.3 to 100 hours, preferably about 0.5 to 20 hours. The reaction temperature is about 0 to 100° C., preferably 0 to 40° C.

The compound obtained in this step can be used in the following reaction step, after being isolated or without isolation.

Reaction Scheme 2

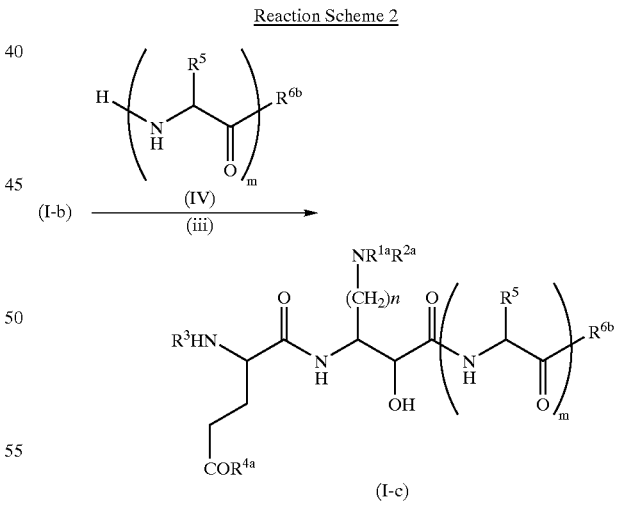

In the formulas, $R^{1a}$, $R^{2a}$, $R^3$, $R^{4a}$, $R^5$, n and m are as defined above; $R^{6b}$ is hydroxyl, lower alkoxy or —$NR^9R^{10}$ (wherein $R^9$ and $R^{10}$ are as defined above), provided, however, that when m is 0, $R^{6b}$ is not hydroxyl.

Examples of the lower alkoxy group represented by $R^{6b}$ include those mentioned as examples of the lower alkoxy group represented by $R^6$.

Step (iii): The compound of formula (I-c) of the invention can be produced by a condensation reaction between the compound of formula (I-b) obtained in Reaction Scheme 1 and a known compound of formula (IV), preferably in a suitable solvent.

The condensation reaction can be carried out by known methods. Useful methods include, for example, a method using a condensing agent such as N,N-dicyclohexylcarbodiimide and 1-ethyl-3-(3-dimethylaminopropyl)carbodiimide hydrochloride or a method using an additive (e.g., 1-hydroxybenzotriazol, N-hydroxy-5-norbornene, etc.) in addition to the condensing agent; the mixed acid anhydride method using isobutyl chloroformate, etc.; the azide method; the active ester method; and the like. Any solvent that does not participate in this reaction can be used. Useful solvents include, for example, N,N-dimethylformamide, tetrahydrofuran, methylene chloride, dioxane, ethyl acetate and N-methylpyrrolidone. These solvents can be used singly or in combinations of two or more. The amount each of the reagents is about 0.5 to 10 moles, preferably 1 to 2 moles, per mole of the compound of formula (II). The reaction time is about 0.3 to 100 hours, preferably about 0.5 to 20 hours. The reaction temperature is about 0° C. to 100° C., preferably 0° C. to 40° C.

The compound obtained in this step can be used in the following reaction step, after being isolated or without isolation.

Reaction Scheme 3

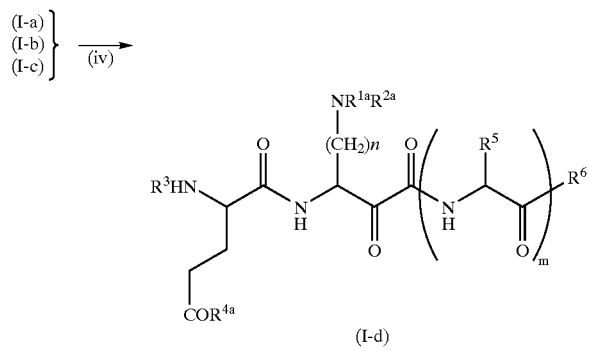

(I-d)

In the formulas, $R^{1a}$, $R^{2a}$, $R^3$, $R^{4a}$, $R^5$, $R^6$, n and m are as defined above.

Step (iv): The compound of formula (I-d) of the invention can be produced by oxidizing a compound of formula (I-a), (I-b) or (I-c) obtained in Reaction Scheme 1 or 2, preferably in a suitable solvent.

The oxidation reaction can be carried out by known methods. Useful methods include, for example, Dess-Martin oxidation using Dess-Martin reagents; and improved Moffat oxidation using dimethyl sulfoxide-1-ethyl-3-(3-dimethylaminopropyl)carbodiimide hydrochloride-dichloroacetic acid. Any solvent can be used in this reaction as long as it does not participate in the reaction. Useful solvents include, for example, N,N-dimethylformamide, tetrahydrofuran, methylene chloride, dioxane, ethyl acetate, N-methylpyrrolidone, etc. These solvents can be used singly or in combinations of two or more. The amount of the reagent is about 0.3 to 100 moles, preferably 1 to 10 moles, per mole of the compound of formula (I-a), (I-b) or (I-c). The reaction time is about 0.1 to 100 hours, preferably about 0.2 to 50 hours. The reaction temperature is about −20° C. to 100° C., preferably 0° C. to 40° C.

The compound obtained in this step can be used in the following reaction step, after being isolated or without isolation.

Reaction Scheme 4

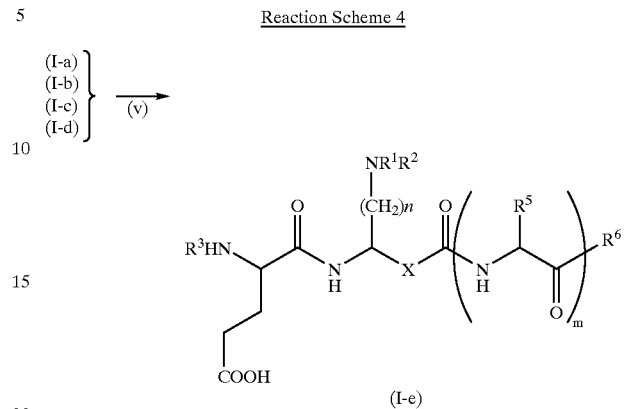

(I-e)

In the formulas, X, $R^3$, $R^{4a}$, $R^5$, $R^6$, n and m are as defined above.

Step (v): The compound of formula (I-e) of the invention can be produced by reacting the compound of formula (I-a), (I-b), (I-c) or (I-d) with an acid, in a suitable solvent or without the use of solvents.

Any solvent can be used in this reaction as long as it does not participate in the reaction. Useful solvents include, for example, chloroform, dichloromethane, dioxane, tetrahydrofuran and ethyl acetate. Useful acids include, for example, mineral acids such as hydrochloric acid and sulfuric acid; and organic acids such as trifluoroacetic acid and p-toluenesulfonic acid. The amount of the acid used in the reaction is about 1 to 1,000 moles, preferably 1 to 100 moles, per mole of the compound of formula (I-a), (I-b), (I-c) or (I-d). The reaction time is about 0.5 to 5 hours. The reaction temperature is about 0° C. to 100° C., preferably 0° C. to 30° C.

Of the compounds of formula (I), the compound wherein $R^4$ is lower alkoxy, optionally substituted piperazinyl or —$NR^7R^8$ (wherein $R^7$ and $R^8$ may be the same or different and are hydrogen, optionally substituted lower alkyl or amino optionally substituted with lower alkyl(s) or phenyl(s)) can be produced in accordance with Reaction Scheme 5 shown below.

Reaction Scheme 5

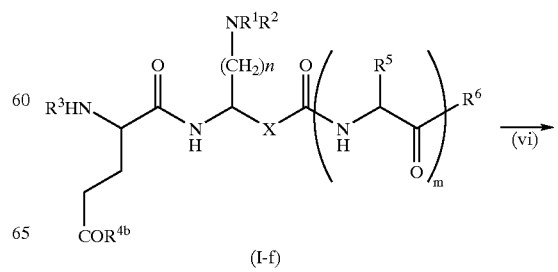

(I-f)

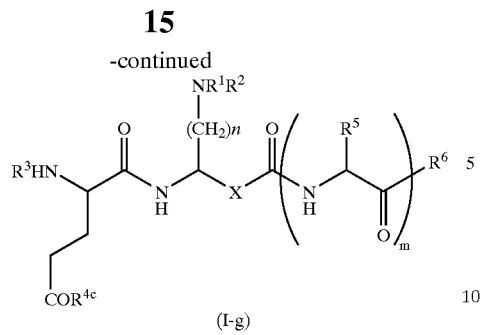

(I-g)

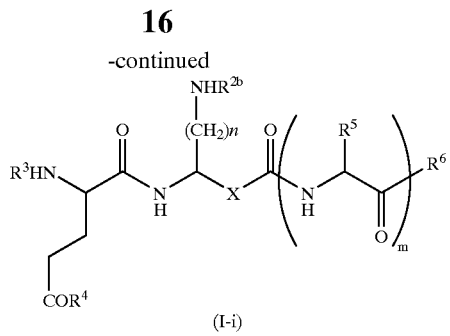

(I-i)

In the formulas, X, $R^1$, $R^2$, $R^3$, $R^5$ $R^6$, n and m are as defined above, $R^{4b}$ is hydroxyl or lower alkoxy, $R^{4c}$ is lower alkoxy, optionally substituted piperazinyl or —$NR^7R^8$ (wherein $R^7$ and $R^8$ are as defined above).

Step (vi): The compound of formula (I-g) of the invention can be produced by reacting compound (I-f) of the invention wherein $R^4$ is hydroxyl with a lower alcohol, optionally substituted piperazine or an amine represented by $NHR^7R^8$ (wherein $R^7$ and $R^8$ are as defined above) using a condensing agent, in a suitable solvent or without the use of solvents.

The condensation reaction can be carried out by known methods. Useful methods include, for example, methods using condensing agents such as N,N-dicyclohexylcarbodiimide and 1-ethyl-3-(3-dimethylaminopropyl)carbodiimide hydrochloride or methods using an additive (e.g., 1-hydroxybenzotriazol, N-hydroxy-5-norbornene-2,3-dicarboxyimide, etc.) in addition to the condensing agent; the mixed acid anhydride method using isobutyl chloroformate, etc.; the azide method; the active ester method; and the like. Any solvent can be used in this reaction as long as it does do not participate in the reactions. Useful solvents include, for example, N,N-dimethylformamide, tetrahydrofuran, methylene chloride, dioxane, ethyl acetate and N-methylpyrrolidone. These solvents can be used singly or in combinations of two or more. As to the amount of the reagents, the lower alcohol, the piperazine or the amine is in an amount of about 0.5 to 10 moles, preferably 1 to 5 moles, per mole of the compound of formula (I-f). The amount of condensing agent is about 0.5 to 10 moles, preferably 1 to 5 moles, and the amount of additive is about 0.5 to 10 moles, preferably 1 to 2 moles, per mole of the compound of formula (I-f). The reaction time is about 0.1 to 100 hours, preferably about 0.3 to 20 hours. The reaction temperature is about 0° C. to 100° C., preferably 0° C. to 40° C.

Of the compounds of formula (I), the compound wherein $R^1$ is hydrogen and $R^2$ is substituted oxycarbonyl can also be produced in accordance with Reaction Scheme 6 shown below.

Reaction Scheme 6

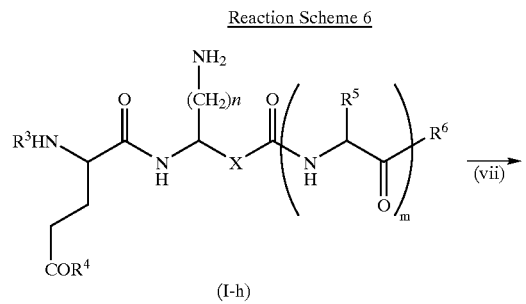

(I-h)

In the formulas, X, $R^3$, $R^4$, $R^5$, $R^6$, n and m are as defined above, and $R^{2b}$ is substituted oxycarbonyl.

Step (vii): The compound of formula (I-i) of the invention can be obtained by protecting the amino group of compound (I-h) of the invention wherein $R^1$ and $R^2$ are hydrogen with a known substituted oxycarbonyl-introducing reagent, preferably in a suitable solvent.

The introducing reagent is not specifically limited as long as it is a known introducing agent used to protect amino groups. Examples of useful introducing reagents include di-tert-butyl dicarbonate, benzyloxycarbonyl chloride, 2,2, 2-trichloroethyloxycarbonyl chloride, and 9-fluorenylmethyloxycarbonyl chloride. Any solvent that does not participate in the reaction can be used. Useful solvents include, for example, N,N-dimethylformamide, tetrahydrofuran, methylene chloride, dioxane, ethyl acetate, N-methylpyrrolidone, etc. These solvents can be used singly or in combinations of two or more. The amount of the protective group introducing reagent is about 1 to 100 moles, preferably 1 to 10 moles, per mole of the compound of formula (I-h). The reaction time is about 0.1 to 100 hours, preferably about 0.5 to 50 hours. The reaction temperature is about −20° C. to 100° C., preferably 0° C. to 40° C. The compound (I-i) obtained in this step can be used for the reactions shown in Reaction Schemes 3 to 5, after being isolated or without isolation.

The compounds of the invention obtained by the above processes and all mentioned compounds can be purified by separation and purification methods usually used in the field of chemical synthesis, such as recrystallization, distillation and various column chromatography methods.

The peptide derivative of formula (1) of the invention and pharmaceutically acceptable salts thereof potently and selectively inhibit KGP, a proteolytic enzyme produced by *P. gingivalis*, which plays a significant role in the onset and progress of periodontal disease. Since the peptide derivative of the invention is composed of a highly safe natural amino acid or a derivative thereof, the derivative, inclusive of its metabolites produced in vivo, is considered to be highly safe.

Therefore, the peptide derivative of formula (I) and pharmaceutically acceptable salts thereof can be used as an active ingredient of Lys-gingipain inhibitors and pharmaceutical preparations for periodontal disease. The Lys-gingipain inhibitors and pharmaceutical preparations for periodontal disease can be used as periodontal preventive agents or therapeutic agents.

The peptide derivative of formula (I) and pharmaceutically acceptable salts thereof can also be used, together with a pharmaceutically acceptable carrier, to prepare compositions for use in the oral cavity. The peptide derivative of formula (I) or pharmaceutically acceptable salts thereof can be mixed with a pharmaceutically acceptable carrier and administered as preparations for use in the oral cavity, such as gel preparations for use in the oral cavity, oral ointments for adhesive application to mucous membranes, oral pastes, periodontal-pocket intercalating agents, and preparations for adhesive application to gingivae; and oral hygiene agents such as toothpastes, mouthwashes, chewing gums, tablets, candies and troches. The compositions for oral cavity can be used as periodontal preventive agents or therapeutic agents.

Useful pharmaceutically acceptable carriers include appropriate carriers commonly used in accordance with the dosage form. Examples of such carriers include methylcellulose, hydroxymethylcellulose, hydroxyethylcellulose, carboxymethylcellulose sodium, hydroxypropylmethylcellulose, liquid paraffin, white petrolatum, Eudoragit L, sodium alginate, propylene glycol alginate, pullulan, tragacanth, xanthan gum, chitosan, polyvinylpyrrolidone, polyvinyl alcohol, polyacrylic acid, sodium polyacrylate, polymethacrylic acid, ethyl methacrylate, dimethylamino acetate, cellulose acetate, collagen, atherocollagen, gelatin, glycerol, triacetin, Macrogol 400, Polysorbate 60, polyoxyl stearate 40, butyl parahydroxybenzoate, ethanol, cetyl alcohol, glyceryl monostearate, calcium carbonate, magnesium carbonate, dibasic calcium phosphate, carrageenan, sodium dioctyl sulfosuccinate, sodium lauryl sulfate, sodium dodecylbenzenesulfonate, hinokitiol, allantoin, glycyrrhizin, gum arabic, starch, cornstarch, saccharin, saccharin sodium, stevioside, glucose, lactose, sorbitol, mannitol, magnesium stearate, potassium phosphate monobasic, potassium phosphate dibasic, menthol, eucalyptus oil, peppermint, spearmint, colors, aromas, sodium fluoride, and fluoride of sodium monofluorophosphate, lysozyme chloride, azulene and like anti-inflammatory agents, sodium chloride and like components usually added.

When a Lys-gingipain inhibitor, pharmaceutical preparation for periodontal disease, or composition for oral cavity, each containing as an active ingredient the peptide derivative of the invention or a pharmaceutically acceptable salt thereof, is to be administered to mammals, including humans, the administration method can be such that an appropriate amount of the inhibitor, preparation or composition having an active ingredient content of 0.001 wt. % or more, preferably 0.01 to 20 wt. %, is inserted, applied or used for washing, etc., usually at least once a day.

When the Lys-gingipain inhibitor, pharmaceutical preparation for periodontal disease, or composition for use in the oral cavity of the invention is used as a therapeutic agent, the dosage can be suitably selected according to the mode of administration, the patient's age, sex and other factors, and the severity of disease. When administered to humans, the dosage of the active ingredient compound of the invention is usually 0.001 to 100 mg per kg body weight a day, preferably 0.005 to 10 mg/kg/day.

When the Lys-gingipain inhibitor, pharmaceutical preparation for periodontal disease or composition for oral cavity of the invention is used as a preventive agent, the dosage can be suitably selected according to the mode of administration, the patient's age, sex and other factors, and the severity of disease. When administered to humans, the dosage of the active ingredient compound of the invention is usually 0.001 to 100 mg per kg body weight a day, preferably 0.005 to 10 mg/kg/day.

BEST MODE FOR CARRYING OUT THE INVENTION

The following Examples and Test Examples are provided to illustrate the invention in detail and are not to limit the scope of the invention. In these examples, Me represents methyl; Boc, t-butoxycarbonyl; Cbz, benzyloxycarbonyl; $^t$Bu, t-butyl; and Ph, phenyl.

EXAMPLE 1

A compound of the following formula was synthesized.

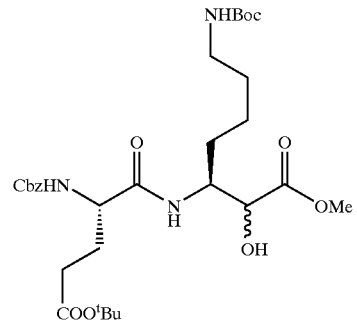

Four grams of 10% palladium-carbon was added to 1000 ml of a mixed solution in methanol-chloroform (10:1) of 21 g (49.47 mmols) of (3S)-7-[(t-butoxy)carbonylamino]-2-hydroxy-3-[(phenylmethoxy)carbonylamino]-heptanoic acid methyl ester (Cbz-Lys(Boc)ψ[CHOHCO]—OMe) which is a known compound prepared by a process described in WO 98/50420. The resulting mixture was stirred in a hydrogen atmosphere at room temperature for 3 hours and 45 minutes, to eliminate benzyloxycarbonyl protective group(s). After completion of the reaction, insoluble matter was filtered off. The filtrate was concentrated, and then, without isolation and purification, dissolved in 525 ml of DMF (dimethylformamide, the same applies hereinafter). Added to this solution with ice-cooling were 20 g (59.36 mmols) of carbobenzoxy-L-glutamic acid γ-t-butylester (Cbz-Glu(O$^t$Bu)-OH), 8.7 g (64.31 mmols) of 1-hydroxybenzotriazole, 11.4 g (59.36 mmols) of 1-ethyl-3-(3-dimethylaminopropyl)carbodiimide hydrochloride and 13.5 g (133.57 mmols) of N-methylmorpholine, followed by stirring at room temperature for 14 hours. After completion of the reaction, a 10% aqueous citric acid solution was added to adjust the pH to 3, followed by extraction with ethyl acetate. The ethyl acetate layer was washed sequentially with a saturated saline solution, a 5% aqueous sodium hydrogen carbonate solution and a saturated saline solution, and dried over anhydrous sodium sulfate. After filtration, the solvent was distilled off, and the residue was separated and purified by silica gel column chromatography (hexane:ethyl acetate=3:2 to 1:1), giving 18.3 g of a diastereomeric mixture of the above compound, as a white powder (yield: 60%). The following are the properties of the mixture.

$^1$H-NMR (DMSO-$d_6$) δ: 7.67 (0.3H, d, J=8.8 Hz), 7.54 (0.7H, d, J=9.0 Hz), 7.40–7.25 (6H, m), 6.73 (1H, m), 5.69 (0.3H, d, J=5.9 Hz), 5.53 (0.7H, d, J=5.6 Hz), 5.02 (2H, m), 4.11–3.96 (3H, m), 3.61 (0.9H, s), 3.56 (2.1H, s), 2.87 (2H, m), 2.20 (2H, m), 1.83 (1H, m), 1.66 (1H, m), 1.59–1.06 (6H, m), 1.38 (9H, s), 1.36 (9H, s).

m.p.: 101–103° C. Mass(FAB(+)): m/z 610 (M+H)$^+$.

EXAMPLE 2

A compound of the following formula was synthesized.

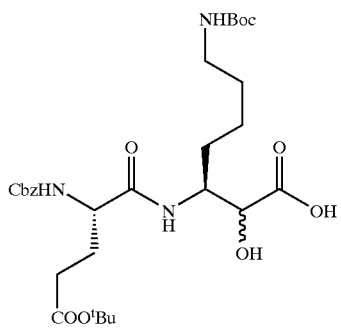

An aqueous solution (10 ml) of 270 mg (6.43 mmols) of lithium hydroxide monohydrate was added to 100 ml of a solution of 3.53 g (5.76 mmols) of the compound obtained in Example 1 in THF (tetrahydrofuran, the same applies hereinafter) with ice cooling. The resulting mixture was stirred for 1 hour, and then stirred at room temperature for 30 minutes. After completion of the reaction, the reaction mixture was concentrated under reduced pressure. A 10% aqueous solution of citric acid was added to the residue to adjust the pH to 3, followed by extraction with ethyl acetate. The ethyl acetate layer was washed with a saturated saline solution, and then dried over anhydrous sodium sulfate. After filtration, the solvent was distilled off, giving 3.5 g of the above compound as a white powder (yield: 100%). The following are the properties of the compound.

$^1$H-NMR (DMSO-$d_6$) δ: 12.45 (1H, brs), 7.49–7.31 (7H, m), 6.74 (1H, m), 5.38 (0.3H, d, J=5.8 Hz), 5.26 (0.7H, d, J=5.8 Hz), 5.01 (1H, ABq, J=12.4 Hz), 4.04–3.85 (4H, m), 2.86 (2H, m), 2.19 (2H, m), 1.90–0.90 (8H, m), 1.40–1.36 (18H, s×2).

m.p.: 48–50° C. Mass(FAB(-)): m/z 594 (M-H)$^-$.

EXAMPLE 3

A compound of the following formula was synthesized.

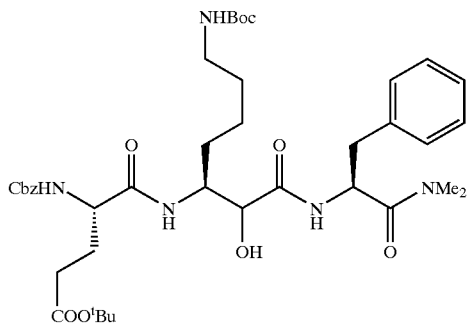

To 5 ml of a DMF solution of 250 mg (0.42 mmols) of the compound obtained in Example 2 were added, with ice cooling, 94 mg (0.420 mmols) of phenylalanine N,N-dimethylamide hydrochloride, 62 mg (0.46 mmols) of 1-hydroxybenzotriazole, 79 mg (0.42 mmols) of 1-ethyl-3-(3-dimethylaminopropyl)carbodiimide hydrochloride and 46 mg (0.46 mmols) of N-methylmorpholine. The resulting mixture was stirred at room temperature for 3 hours. After completion of the reaction, a 10% aqueous solution of citric acid was added to adjust the pH to 3, followed by extraction with ethyl acetate. The ethyl acetate layer was washed sequentially with a saturated saline solution, a 5% aqueous solution of sodium hydrogen carbonate, and a saturated saline solution, and then dried over anhydrous sodium sulfate. After filtration, the solvent was distilled off, and the residue was separated and purified by silica gel column chromatography (hexane:ethyl acetate:methanol=5:5:1), giving diastereomers of the above compound as white powders in amounts of 93 mg (yield: 31%) and 60 mg (yield: 20%) in the order of elution. The following are the properties of the diastereomers.

First Eluted Diastereomer $^1$H-NMR (DMSO-$d_6$) δ: 7.88 (1H, d, J=8.1 Hz), 7.40 (1H, d, J=8.0 Hz), 7.35–7.20 (11H, m), 6.73 (1H, t, J=5.4 Hz), 5.75 (1H, d, J=6.1 Hz), 5.00 (2H, ABq, J=12.4 Hz), 4.88 (1H, dt, J=9.4, 4.7 Hz), 4.07–3.85 (3H, m), 2.95–2.80 (4H, m), 2.74 (6H, s×2), 2.18 (2H, t, J=7.7 Hz), 1.83 (1H, m), 1.66 (1H, m), 1.49–1.11 (6H, m), 1.36 (18H, s×2).

m.p.: 68–71° C. Mass(FAB(+)): m/z 770 (M+H)$^+$, Mass (FAB(-)): m/z 768 (M-H)$^-$.

Second Eluted Diastereomer $^1$H-NMR (DMSO-$d_6$) δ: 7.68 (1H, d, J=8.5 Hz), 7.49 (1H, d, J=9.0 Hz), 7.41–7.14 (11H, m), 6.72 (1H, t, J=5.1 Hz), 5.92 (1H, d, J=5.8 Hz), 5.02 (2H, ABq, J=12.4 Hz), 4.98 (1H, m), 4.04–3.96 (2H, m), 3.84 (1H, m), 2.95–2.73 (4H, m), 2.87 (3H, s), 2.79 (3H, s), 2.21 (2H, t, J=8.0 Hz), 1.89 (1H, m), 1.72 (1H, m), 1.48–0.83 (6H, m), 1.38 (9H, s), 1.36 (9H, s).

m.p.: 132–134° C. Mass(FAB(+)): m/z 770 (M+H)$^+$, Mass(FAB(-m/z 768 (M-H)$^-$.

In the following Examples 4 to 11, the compounds shown therein were synthesized by following the procedure of Example 3.

EXAMPLE 4

A compound of the following formula was synthesized, and its diastereomers were separated.

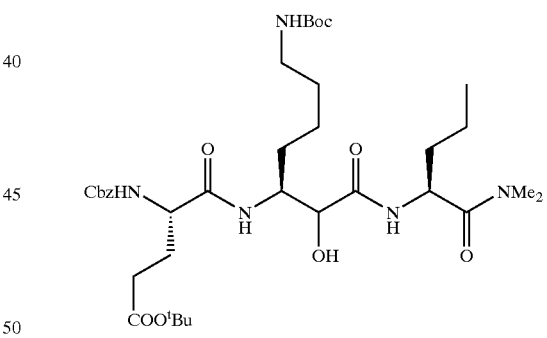

First Eluted Diastereomer $^1$H-NMR (DMSO-$d_6$) δ: 7.76 (1H, d, J=8.3 Hz), 7.40 (1H, d, J=7.8 Hz), 7.36–7.32 (6H, m), 6.72 (1H, t, J=5.1 Hz), 5.69 (1H, d, J=2.9 Hz), 5.02 (2H, s), 4.74 (1H, m), 4.04–3.86 (3H, m), 3.00 (3H, s), 2.81 (3H, s), 2.89–2.81 (2H, m), 2.18 (2H, t, J=7.5 Hz), 1.84 (1H, m), 1.70–1.16 (10H, m), 1.37 (9H, s ), 1.36 (9H, s ), 0.87 (3H, d, J=6.3 Hz), 0.85 (3H, d, J=6.8 Hz).

m.p.: 59–61° C. Mass(FAB(+)): m/z 736 (M+H)$^+$.

Second Eluted Diastereomer $^1$H-NMR (DMSO-$d_6$) δ: 7.65 (1H, d, J=8.5 Hz), 7.56 (1H, d, J=8.6 Hz), 7.41 (1H, d, J=7.8 Hz), 7.37–7.31 (5H, m), 6.72 (1H, t, J=5.9 Hz), 5.96 (1H, d, J=5.6 Hz), 5.03 (2H, ABq, J=12.4 Hz), 4.80 (1H, dt, J=3.8, 9.5 Hz), 4.11–3.99 (2H, m), 3.88 (1H, m), 3.02 (3H, s), 2.83 (3H, s), 2.85–2.79 (2H, m), 2.21 (2H, t, J=8.1 Hz), 1.88 (1H, m), 1.70 (1H, m), 1.61–1.00 (9H, m), 1.38 (9H, s), 1.35 (9H, s), 0.91 (3H, d, J=6.8 Hz), 0.86 (3H, d, J=6.8 Hz).

m.p.: 155–157° C. Mass(FAB(+)): m/z 736 (M+H)⁺.

EXAMPLE 5

A compound of the following formula was obtained as a diastereomeric mixture.

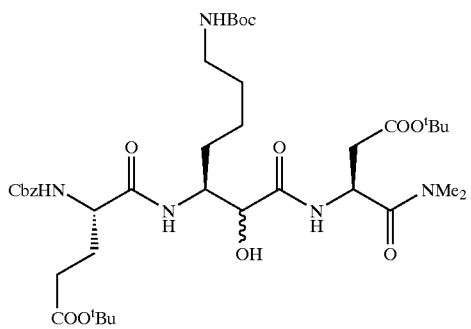

$^1$H-NMR (DMSO-$d_6$) δ: 7.77 & 7.74 (1H, d, J=7.8, 8.8 Hz), 7.58–7.26 (7H, m), 6.72 (1H, m), 5.95 & 5.81 (1H, d, J=6.6, 5.8 Hz), 5.05–4.97 (2H, m), 4.83–4.67 (1H, m), 4.14–3.86 (3H, m), 3.05 & 3.02 (3H, s), 2.86–2.56 (2H, m), 2.83 & 2.82 (3H, s), 2.21–2.15 (4H, m), 1.93–1.77 (2H, m), 1.73–1.56 (2H, m), 1.44–1.09 (6H, m), 1.41–1.35 (27H, m).

m.p.: 58–60° C. Mass(FAB(+)): m/z 808 (M+H)⁺, 830 (M+Na)⁺.

EXAMPLE 6

A compound of the following formula was obtained as a diastereomeric mixture.

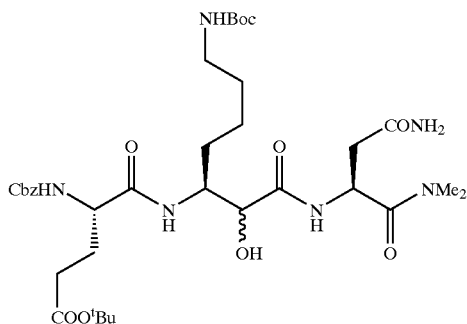

$^1$H-NMR (DMSO-$d_6$) δ: 7.78 & 7.79 (1H, d, J=8.8 & 8.0 Hz), 7.53 & 7.41 (1H, d, J=9.2 & 8.0 Hz), 7.35–7.25 (7H, m), 6.83–6.69 (2H, m), 5.86 & 5.72 (1H, d, J=5.6 & 6.0 Hz), 5.01 (2H, s), 5.04–5.01 (1H, m), 4.02–3.80 (3H, m), 3.02 & 2.98 (3H, s), 2.80 & 2.78 (3H, s), 2.90–2.75 (2H, m), 2.60–2.49 (1H, m), 2.40–2.20 (3H, m), 1.90–0.95 (6H, m), 1.37 (9H, s), 1.35 (9H, s).

m.p.: 88–91° C. Mass(FAB(+)): m/z 737 (M+H)⁺, 759 (M+Na)⁺.

EXAMPLE 7

A compound of the following formula was obtained as a diastereomeric mixture.

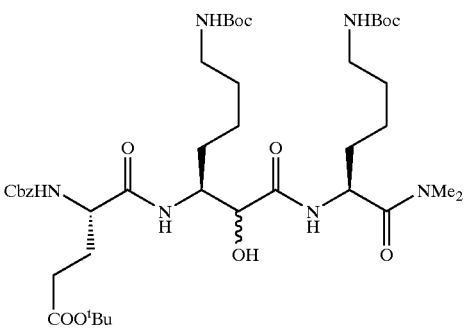

$^1$H-NMR (DMSO-$d_6$) δ: 7.77 & 7.68 (1H, d, J=8.3 & 8.0 Hz), 7.57–7.24 (7H, m), 6.78–6.63 (2H, m), 5.95 & 5.72 (1H, d, J=5.8 Hz), 5.07–4.96 (2H, m), 4.77–4.61 (1H, m), 4.12–3.84 (3H, m), 3.03 & 3.00 (3H, s), 2.89–2.80 (4H, m), 2.83 & 2.82 (3H, s), 2.19 (2H, m), 1.93–0.99 (14H, m), 1.35–1.38 (27H, s×3).

Mass(FAB(+)): m/z 851 (M+H)⁺, 873 (M+Na)⁺.

State: foamed material

EXAMPLE 8

A compound of the following formula was obtained as a diastereomeric mixture.

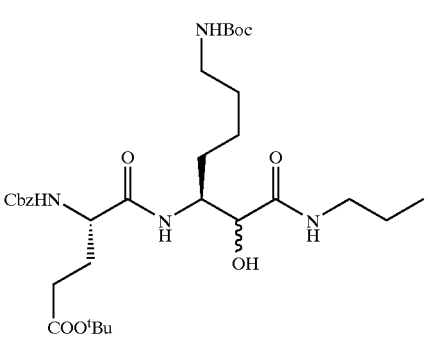

$^1$H-NMR (DMSO-$d_6$) δ: 7.63 (1H, t, J=5.9 Hz), 7.45–7.20 (7H, m), 6.80–6.65 (1H, m), 5.83 & 5.76 (1H, d, J=6.1, 5.6 Hz), 5.03 & 5.02 (2H, s), 4.10–3.93 (2H, m), 3.85 (1H, m), 3.02 (2H, m), 2.84 (2H, m), 2.18 (2H, m), 1.95–1.59 (2H, m), 1.58–1.06 (8H, m), 1.38 & 1.36 & 1.35 (18H, s×2), 0.82 & 0.80 (3H, t, J=7.3 Hz).

m.p.: 73–75° C. Mass(FAB(+)): m/z 659 (M+Na)⁺.

EXAMPLE 9

A compound of the following formula was synthesized, and its diastereomers were separated.

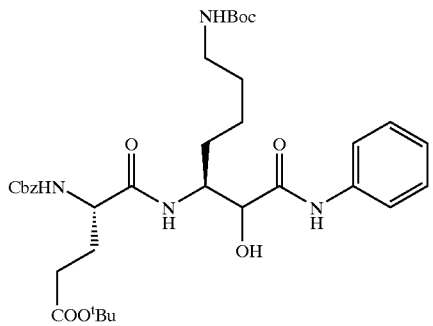

First Eluted Diastereomer $^1$H-NMR (DMSO-d$_6$) δ: 9.62 (1H, s), 7.68 (2H, d. J=7.8 Hz), 7.62 (1H, d, J=6.4 Hz), 7.42 (1H, d, J=8.1 Hz), 7.36–7.27 (7H, m), 7.06 (1H, t, J=7.5 Hz), 6.69 (1H, t, J=5.0 Hz), 6.05 (1H, d, J=5.8 Hz), 5.02 (2H, ABq, J=12.6 Hz), 4.17–4.00 (3H, m), 2.91–2.82 (2H, m), 2.21 (2H, t, J=7.8 Hz), 1.94–1.81 (1H, m), 1.76–1.62 (1H, m), 1.56–1.01 (6H, m), 1.38 (9H, s), 1.34 (9H, s).

m.p.: 150–153° C. Mass(FAB(+)): m/z 671 (M+H)$^+$, 693 (M+Na)$^+$.

Second Eluted Diastereomer $^1$H-NMR (DMSO-d$_6$) δ: 9.51 (1H, s), 7.61 (2H, d. J=7.6 Hz), 7.48 (1H, d, J=9.0 Hz), 7.40 (1H, d, J=8.3 Hz), 7.35–7.24 (7H, m), 7.04 (1H, t, J=7.4 Hz), 6.75 (1H, m), 6.00 (1H, d, J=5.6 Hz), 4.99 (2H, s), 4.13–3.93 (3H, m), 2.90–2.85 (2H, m), 2.10 (2H, t, J=7.8 Hz), 1.86–1.76 (1H, m), 1.66–1.57 (1H, m), 1.48–1.12 (6H, m), 1.36 (9H, s), 1.33 (9H, s).

m.p.: 146–147° C. Mass(FAB(+)): m/z 671 (M+H)$^+$, 693 (M+Na)$^+$.

EXAMPLE 10

A compound of the following formula was obtained as a diastereomeric mixture.

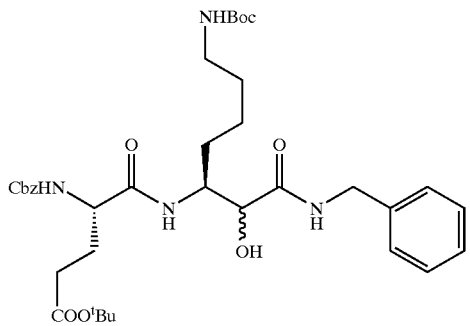

$^1$H-NMR (DMSO-d$_6$) δ: 8.21 (1H, t, J=6.1 Hz), 7.95–7.19 (12H, m), 6.75 (1H, m), 5.87 (1H, d, J=5.6 Hz), 5.01 (2H, s), 4.33 (1H, dd, J=6.8, 15.2 Hz), 4.19 (1H, dd. J=6.0, 15.2 Hz), 4.04–3.92 (3H, m), 2.86 (2H, m), 2.19 (2H, m), 1.97–1.60 (2H, m), 1.59–1.16 (6H, m), 1.36 (18H, s×2).

m.p.: 111–113° C.

EXAMPLE 11

A compound of the following formula was obtained as a diastereomeric mixture.

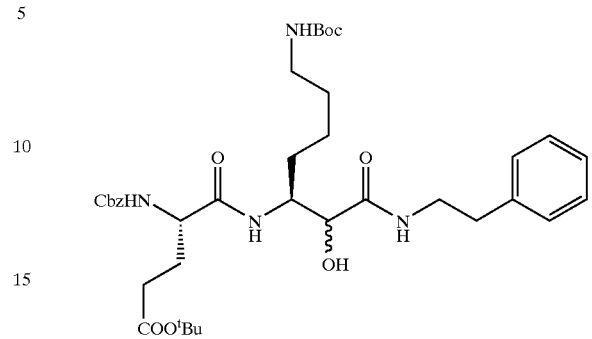

$^1$H-NMR (DMSO-d$_6$) δ: 7.81 & 7.73 (1H, t, J=5.7 Hz), 7.45–7.15 (12H, m), 6.71 (1H, m), 5.86 & 5.76 (1H, m), 5.01 & 5.01 (2H, s), 4.07–3.94 (2H, m), 3.84 (1H, m), 3.30 (2H, m), 2.86 (2H, m), 2.69 (2H, t, J=7.8 Hz), 2.18 (2H, m), 1.94–1.59 (2H, m), 1.56–1.01 (6H, m), 1.36 & 1.35 & 1.32 (18H, s×2).

m.p.: 82–85° C. Mass(FAB(+)): m/z 721 (M+Na)$^+$.

Among the compounds represented by Formula (I), those in which R$^4$ is amide or hydrazide were synthesized by the process shown below.

EXAMPLE 12

A compound of the following formula was synthesized.

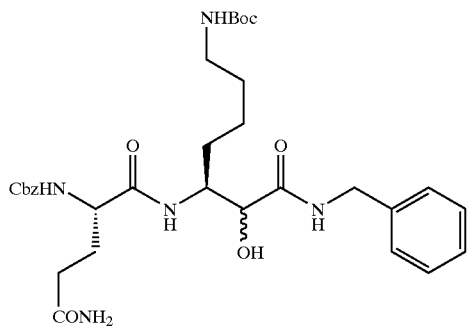

To 5.60 g (8.18 mmols) of the compound obtained in Example 10 were added 200 ml of a 4N hydrochloric acid-ethyl acetate solution and 100 ml of methanol. The resulting mixture was stirred at room temperature for 3 hours and 20 minutes. After distilling off the solvent, 100 ml of a saturated aqueous solution of sodium hydrogen carbonate was added to the residue to adjust the pH to 8. Thereafter, 100 ml of a THF solution of 2.65 g (12.14 mmols) of di-tert-butyl dicarbonate were added, followed by stirring at room temperature for 17 hours. After completion of the reaction, ethyl acetate was added for extraction. The organic layer was washed with a saturated saline solution, and then dried over anhydrous sodium sulfate. After filtration, the solvent was distilled off, giving 4.42 g of white crystals (yield: 84%). Two grams (3.18 mmols) of the crystals were dissolved in 15 ml of THF. To the resulting solution were added, with ice cooling, 1 ml of an aqueous solution of 144 mg (3.43 mmols) of lithium hydroxide monohydrate and 1 ml of methanol, followed by stirring at room temperature for 45 minutes. After completion of the reaction, a 10% aqueous solution of citric acid was added to the residue to adjust the pH to 3, followed by extraction with ethyl acetate. The ethyl acetate layer was washed with a saturated saline solution and dried over anhydrous sodium sulfate. After filtration, the solvent was distilled off, giving 1.4 g of a foamed material (yield: 72%). Isobutyl chlorocarbonate (43 μl) and N-methylmorpholine (37 μl) were added to a THF solution (5 ml) of 200 mg (0.318 mmols) of the foamed material with ice cooling, followed by stirring for 15 minutes. Then, 30 μl of a 28% aqueous ammonia solution was added, followed by stirring for a further 30 minutes. After completion of the reaction, a 10% aqueous citric acid solution was added, followed by extraction with ethyl acetate. The ethyl acetate layer was washed sequentially with a saturated saline solution, a 5% aqueous sodium hydrogen carbonate solution and a saturated saline solution, and then dried over anhydrous sodium sulfate. After filtration, the solvent was distilled off, giving 187 mg of a diastereomeric mixture of the above compound as a white powder (yield: 94%). The following are the properties of the diastereomeric mixture.

$^1$H-NMR (DMSO-$d_6$) δ: 8.35 (0.4H, t, J=6.2 Hz), 8.21 (0.6H, d, J=6.0 Hz), 7.60 (0.4H, d, J=8.8 Hz), 7.52 (12.6H, m), 6.83–6.67 (2H, m), 5.88 (0.4H, d, J=5.1 Hz), 5.82 (0.6H, d, J=5.4 Hz), 5.03 & 5.01 (2H, s), 4.38–3.88 (5H, m), 2.93–2.74 (2H, m), 2.24–2.03 (2H, m), 1.93–1.66 (2H, m), 1.60–1.16 (6H, m), 1.37 (9H, s).

m.p.: 138–141° C. Mass(FAB(+)): m/z 650 (M+Na)$^+$.

In the following Examples 13 to 17, the compounds shown therein were synthesized by following the procedure of Example 12 and using corresponding amines.

EXAMPLE 13

A compound of the following formula was obtained as a diastereomeric mixture.

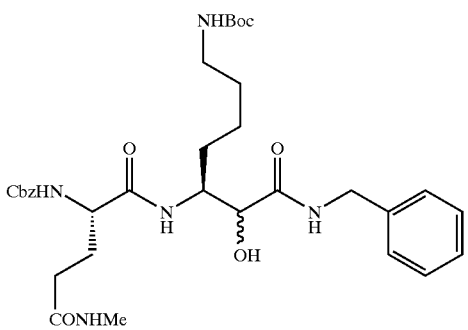

$^1$H-NMR (DMSO-$d_6$) δ: 8.35 (0.4H, t, J=6.1 Hz), 8.22 (0.6H, t, J=6.1 Hz), 7.78–7.17 (13H, m), 6.80–6.66 (1H, m), 5.88 & 5.80 (1H, d, J=5.8 Hz), 5.08–4.94 (2H, m), 4.38–3.86 (5H, m), 2.92–2.74 (2H, m), 2.54 (3H, d, J=4.4 Hz), 2.29–2.01 (2H, m), 1.95–0.98 (8H, m), 1.37 (9H, s).

m.p.: 147–149° C. Mass(FAB(+)): m/z 680 (M+K)$^+$.

EXAMPLE 14

A compound of the following formula was obtained as a diastereomeric mixture.

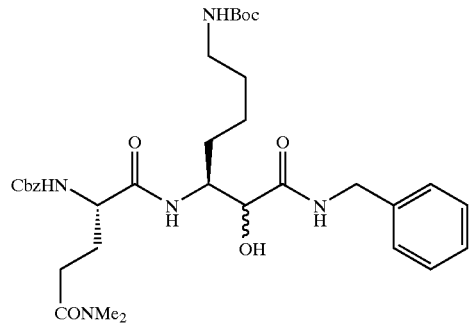

$^1$H-NMR (DMSO-$d_6$) δ: 8.34 (0.4H, t, J=6.1 Hz), 8.21 (0.6H, t, J=6.0 Hz), 7.58–7.06 (12H, m), 6.79–6.66 (1H, m), 5.85 (0.6H, d, J=5.6 Hz), 5.80 (0.4H, t, J=5.4 Hz), 5.03–5.01 (2H, m), 4.34–3.94 (5H, m), 2.91 & 2.89 (3H, s), 2.79 & 2.78 (3H, s), 2.89–2.73 (2H, m), 2.35–2.21 (2H, m), 1.92–1.66 (2H, m), 1.58–1.01 (6H, m), 1.37 (9H, s).

Mass(FAB(+)): m/z 656 (M+H)$^+$, 678 (M+Na)$^+$.

State: foamed material.

EXAMPLE 15

A compound of the following formula was obtained as a diastereomeric mixture.

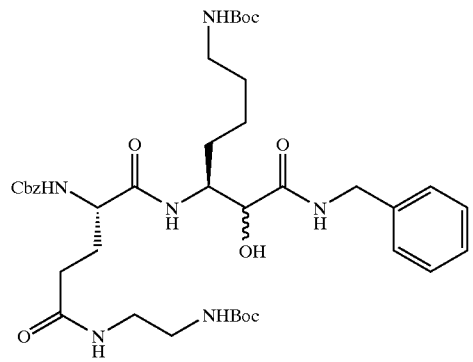

$^1$H-NMR (DMSO-$d_6$) δ: 8.34 (0.3H, t, J=5.9 Hz), 8.21 (0.7H, t, J=6.3 Hz), 7.83–7.70 (1H, m), 7.60–7.21 (12H, m), 6.81–6.66 (2H, m), 5.90 (0.7H, d, J=5.2 Hz), 5.83 (0.3H, d, J=5.6 Hz), 5.02 & 5.01 (2H, s), 4.29–3.85 (5H, m), 3.03–2.75 (6H, m), 2.20–2.05 (2H, m), 1.99–1.60 (2H, m), 1.60–1.16 (6H, m), 1.36 (18H, s).

m.p.: 170–172° C. Mass(FAB(+)): m/z 793 (M+Na)$^+$.

EXAMPLE 16

A compound of the following formula was obtained as a diastereomeric mixture.

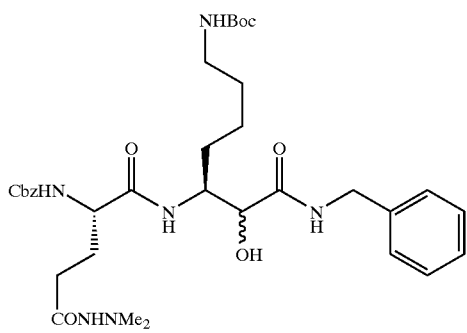

$^1$H-NMR (DMSO-$d_6$) δ: 8.97 (1H, brs), 8.38–8.30 (1H, m), 8.25 (1H, d, J=6.8 Hz), 7.60–7.19 (11H, m), 6.77 (1H, m), 5.97–5.74 (1H, m), 5.04 & 5.01 (2H, s), 4.34–4.20 (2H, m), 4.19–3.94 (3H, m), 2.90–2.67 (2H, m), 2.48 (3H, s), 2.40 (3H, s), 2.15–1.95 (2H, m), 1.94–0.95 (8H, m), 1.37 (9H, s).

m.p.: 123–125° C. Mass(FAB(+)): m/z 671 (M+H)$^+$, 693 (M+Na)$^+$, 709 (M+K)$^+$.

EXAMPLE 17

A compound of the following formula was obtained as a diastereomeric mixture.

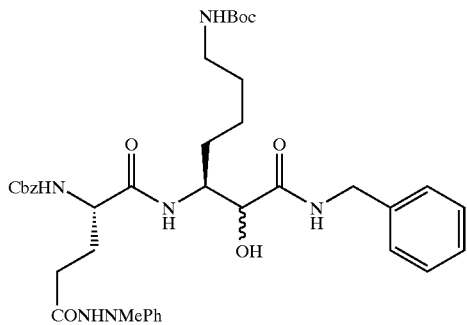

$^1$H-NMR (DMSO-$d_6$) δ: 9.86 (1H, s), 8.35 & 8.23 (1H, t, J=6.1 Hz), 7.62–7.14 (14H, m), 6.72 (3H, m), 5.89 & 5.81 (1H, d, J=5.5 Hz), 5.06–4.98 (2H, m), 4.34–3.94 (5H, m), 3.06 & 3.05 (3H, s), 2.96–2.71 (2H, m), 2.31–2.10 (2H, m), 1.98–1.62 (2H, m), 1.60–1.21 (7H, m), 1.37 (9H, s).

m.p.: 170–173° C. Mass(FAB(+)): m/z 771 (M+K)$^+$.

EXAMPLE 18

A compound of the following formula was synthesized.

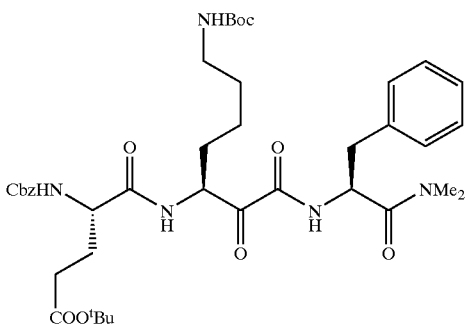

Dess-Martin reagent (83 mg, 0.195 mmols) was added to 3 ml of a methylene chloride solution of 100 mg (0.130 mmols) of the compound obtained in Example 3, followed by stirring at room temperature for 15 minutes. After completion of the reaction, a 20% aqueous solution of sodium hydrogen sulfite was added. The mixture was stirred for 5 minutes and subjected to extraction with ethyl acetate. The ethyl acetate layer was washed sequentially with a saturated saline solution, a 5% aqueous sodium hydrogen carbonate solution and a saturated saline solution, and then dried over anhydrous sodium sulfate. After filtration, the solvent was distilled off, and the residue was separated and purified by silica gel column chromatography (hexane:ethyl acetate=2:3), giving 56 mg of the above compound as a white powder (yield: 56%). The following are the properties of the compound.

$^1$H-NMR (DMSO-$d_6$) δ: 8.79 (1H, d, J=8.5 Hz), 8.18 (1H, d, J=6.8 Hz), 7.39 (1H, d, J=8.3 Hz), 7.36–7.17 (10H, m), 6.78 (1H, t, J=5.6 Hz), 5.01 (2H, ABq, J=12.4 Hz), 4.94 (1H, dt, J=7.0, 8.3 Hz), 4.85 (1H, m), 4.05 (1H, m), 2.98 (1H, dd, J=5.6, 13.8 Hz), 3.33 (3H, s), 2.93 (3H, s), 2.91 (1H, dd, J=9.0, 13.7 Hz), 2.88–2.74 (2H, m), 2.25 (2H, t, J=8.0 Hz), 1.91–1.64 (2H, m), 1.39 (9H, s), 1.37 (9H, s), 1.34–1.15 (6H, m).

m.p.: 102–104° C. Mass(FAB(+)): m/z 768 (M+H)$^+$, 806 (M+K)$^+$.

In the following Examples 19 to 33, compounds shown therein were synthesized by following the procedure of Example 18.

EXAMPLE 19

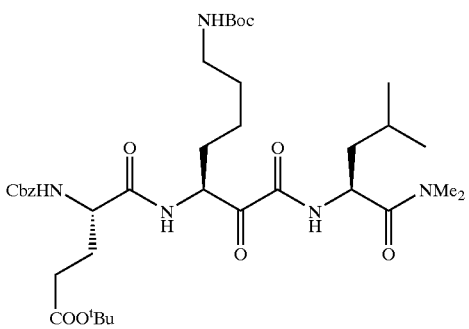

$^1$H-NMR (DMSO-$d_6$) δ: 8.64 (1H, d, J=8.3 Hz), 8.24 (1H, d, J=6.6 Hz), 7.41 (1H, d, J=8.3 Hz), 7.39–7.26 (5H, m), 6.76 (1H, t, J=5.0 Hz), 5.02 (2H, ABq, J=12.7 Hz), 4.95 (1H, m), 4.75 (1H, m), 4.07 (1H, m), 3.03 (3H, s), 2.87 (2H, m), 2.83 (3H, s), 2.26 (2H, t, J=7.8 Hz), 1.94–1.19 (11H, m), 1.39 (9H, s), 1.36 (9H, s), 0.89 (3H, d, J=6.6 Hz), 0.86 (3H, d, J=6.6 Hz).

m.p.: 119–122° C. Mass(FAB(+)): m/z 734 (M+H) 756 (M+Na)⁺.

EXAMPLE 20

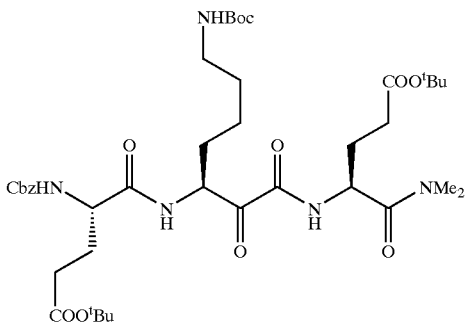

¹H-NMR (DMSO-d₆) δ: 8.64 (1H, d, J=8.3 Hz), 8.25 (1H, d, J=6.8 Hz), 7.41 (1H, d, J=8.3 Hz), 7.35–7.27 (5H, m), 6.76 (1H, t, J=4.5 Hz), 5.01 (2H, ABq, J=12.5 Hz), 4.96 (1H, m), 4.80 (1H, m), 4.07 (1H, m), 3.05 (3H, s), 2.92–2.88 (2H, m), 2.93 (3H, s), 2.31–2.16 (4H, m), 1.99–1.65 (4H, m), 1.55–1.24 (6H, m), 1.39 (18H, s×2), 1.36 (9H, s).

m.p.: 127–130° C. Mass(FAB(+)): m/z 806 (M+H)⁺, 828 (M+Na)⁺.

EXAMPLE 21

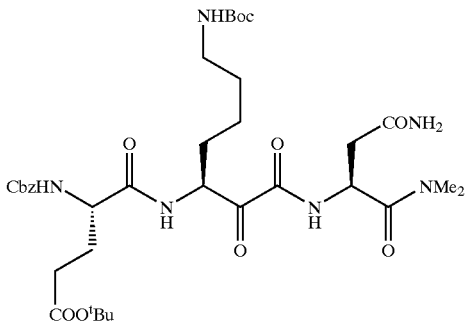

¹H-NMR (DMSO-d₆) δ: 8.89 (1H, t, J=8.6 Hz), 8.25 (1H, d, J=6.8 Hz), 7.41 (1H, d, J=8.3 Hz), 7.36–7.32 (6H, m), 6.86 (1H, m), 6.77 (1H, m), 5.02–4.95 (4H, m), 4.05 (1H, m), 3.02 (3H, s), 2.87–2.81 (2H, m), 2.81 (3H, s), 2.61 (1H, dd, J=7.3, 15.4 Hz), 2.36 (1H, dd, J=6.6, 15.2 Hz), 2.23–2.18 (2H, m ), 1.91–1.68 (3H, m), 1.51–1.20 (5H, m), 1.39 (9H, s), 1.36 (9H, s).

m.p.: 122–124° C. Mass(FAB(+)): m/z 735 (M+H)⁺, 757 (M+Na)⁺.

EXAMPLE 22

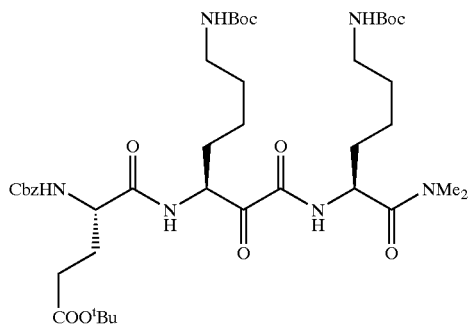

¹H-NMR (DMSO-d₆) δ: 8.57 (1H, d, J=8.1 Hz), 8.25 (1H, d, J=6.6 Hz), 7.40 (1H, d, J=8.5 Hz), 7.35–7.25 (5H, m), 6.75 (2H, t, J=5.1 Hz), 5.01 (2H, ABq, J=13.0 Hz), 4.98–4.91 (1H, m), 4.72–4.61 (1H, m), 4.08 (1H, dt, J=8.3, 5.4 Hz), 3.05 (3H, s), 2.93–2.83 (4H, m), 2.83 (3H, s), 2.24 (2H, t, J=8.3 Hz), 1.99–0.80 (14H, m), 1.39 (9H, s), 1.36 (18H, s×2).

m.p.: 152–155° C. Mass(FAB(+)): m/z 849 (M+H)⁺.

EXAMPLE 23

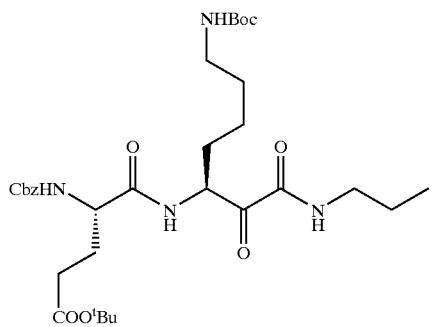

¹H-NMR (DMSO-d₆) δ: 8.68 (1H, t, J=6.1 Hz), 8.26 (1H, d, J=6.6 Hz), 7.40 (1H, d, J=8.6 Hz), 7.35–7.31 (5H, m), 6.76 (1H, t, J=5.5 Hz), 5.01 (2H, ABq, J=12.7 Hz), 4.92–4.87 (1H, m), 4.09–4.02 (1H, m), 3.10–3.04 (2H, m), 2.93–2.82 (2H, m), 2.25 (2H, t, J=8.1 Hz), 1.92–1.16 (10H, m), 1.39 (9H, s), 1.36 (9H, s), 0.82 (3H, t, J=7.4 Hz).

m.p.: 131–133° C. Mass(FAB(+)): m/z 673 (M+K)⁺.

EXAMPLE 24

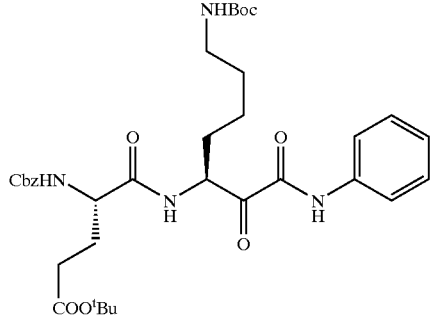

¹H-NMR (DMSO-d₆) δ: 10.58 (1H, s), 8.41 (1H, d, J=6.1 Hz), 7.79 (2H, d, J=8.8 Hz), 7.43 (1H, d, J=8.1 Hz), 7.40–7.25 (7H, m), 7.13 (1H, t, J=7.3 Hz), 6.77 (1H, m), 5.01 (2H, ABq, J=12.7 Hz), 5.01 (1H, m), 4.08 (1H, m), 2.90 (2H, m), 2.26 (2H, t, J=7.8 Hz), 1.95–1.65 (3H, m), 1.64–1.49 (1H, m), 1.48–1.10 (4H, m), 1.38 (9H, s), 1.36 (9H, s).

m.p.: 134–136° C.

EXAMPLE 25

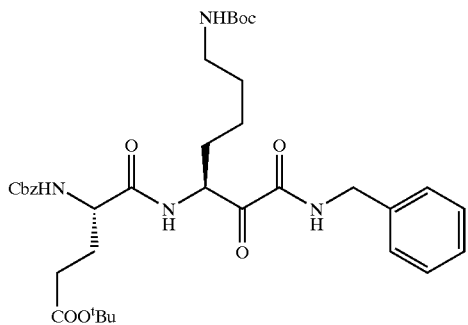

$^1$H-NMR (DMSO-$d_6$) δ: 9.24 (1H, t, J=6.3 Hz), 8.30 (1H, d, J=6.6 Hz), 7.41 (1H, d, J=8.3 Hz), 7.36–7.21 (10H, m), 6.77 (1H, t, J=5.4 Hz), 5.01 (2H, ABq, J=12.7 Hz), 4.96–4.90 (1H, m), 4.32 (2H, dq, J=6.2, 14.9 Hz), 4.08 (1H, dt, J=6.0, 8.6 Hz), 2.92–2.83 (2H, m), 2.25 (2H, t, J=8.0 Hz), 1.91–1.15 (8H, m), 1.38 (9H, s), 1.36 (9H, s).

m.p.: 130–132° C. Mass(FAB(+)): m/z 705 (M+Na)$^+$.

EXAMPLE 26

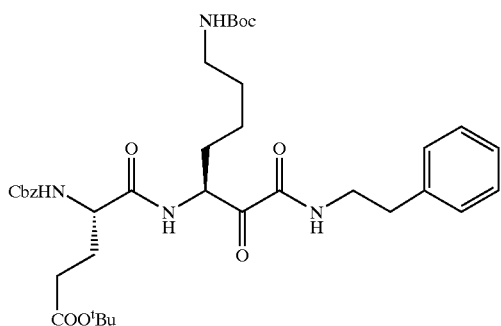

$^1$H-NMR (DMSO-$d_6$) δ: 8.76 (1H, t, J=5.9 Hz), 8.24 (1H, d, J=6.4 Hz), 7.41 (1H, d, J=8.0 Hz), 7.40–7.16 (10H, m), 6.77 (1H, t, J=4.9 Hz), 5.01 (2H, ABq, J=12.7 Hz), 4.91 (1H, m), 4.06 (1H, m), 3.35 (2H, m), 2.88 (2H, m), 2.75 (2H, m), 2.25 (2H, t, J=7.9 Hz), 1.93–1.08 (8H, m), 1.38 (9H, s), 1.37 (9H, s).

m.p.: 148–150° C. Mass(FAB(+)): m/z 697 (M+H)$^+$.

EXAMPLE 27

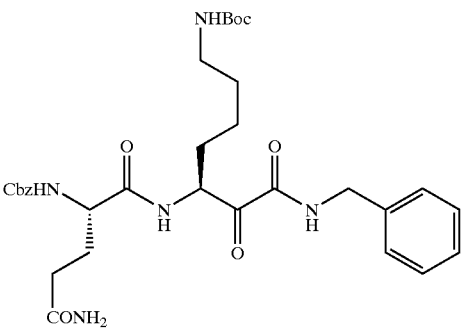

$^1$H-NMR (DMSO-$d_6$) δ: 9.25 (1H, t, J=6.3 Hz), 8.29 (1H, d, J=6.8 Hz), 7.41–7.24 (12H, m), 6.77–6.70 (2H, m), 5.02 (2H, s), 5.02–4.97 (1H, m), 4.34 (2H, dq, J=6.4, 12.7 Hz), 4.12–4.04 (1H, m), 2.88–2.84 (2H, m), 2.20–2.02 (2H, m), 1.95–1.58 (2H, m), 1.57–1.10 (6H, m), 1.36 (9H, s).

m.p.: 193–195° C. Mass(FAB(+)): m/z 664 (M+K)$^+$.

EXAMPLE 28

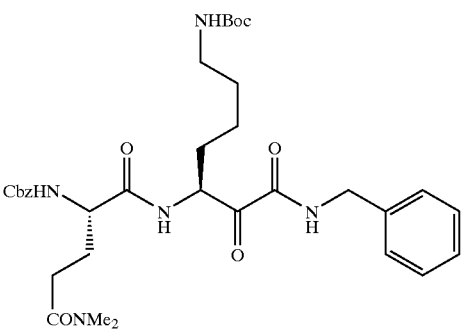

$^1$H-NMR (DMSO-$d_6$) δ: 9.24 (1H, t, J=6.1 Hz), 8.28 (1H, t, J=6.0 Hz), 7.70 (1H, brs), 7.43–7.18 (11H, m), 6.76 (1H, m), 5.02 (2H, s), 5.00–4.92 (1H, m), 4.37–4.24 (2H, m), 4.11–3.98 (1H, m), 2.93–2.79 (2H, m), 2.54 (3H, d, J=4.6 Hz), 2.21–2.02 (2H, m), 2.00–1.62 (3H, m), 1.55–1.17 (5H, m), 1.36 (9H, s).

m.p.: 189–192° C. Mass(FAB(+)): m/z 640 (M+H)$^+$.

EXAMPLE 29

$^1$H-NMR (DMSO-$d_6$) δ: 9.24 (1H, t, J=6.2 Hz), 8.31 (1H, t, J=6.4 Hz), 7.44 (1H, d, J=8.0 Hz), 7.35–7.22 (10H, m), 6.76 (1H, t, J=5.1 Hz), 5.01 (2H, s), 5.05–4.97 (1H, m), 4.37–4.26 (2H, m), 4.08–4.00 (1H, m), 2.92 (3H, s), 2.93–2.88 (2H, m), 2.80 (3H, s), 2.36–2.32 (2H, m), 1.84–1.74 (3H, m), 1.52–1.23 (5H, m), 1.36 (9H, s).

m.p.: 98–101° C.

EXAMPLE 30

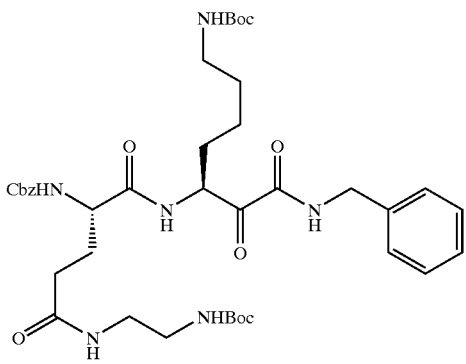

$^1$H-NMR (DMSO-d$_6$) δ: 9.24 (1H, t, J=6.1 Hz), 8.29 (1H, d, J=6.8 Hz), 7.79 (1H, t, J=5.4 Hz), 7.45–7.18 (11H, m), 6.81–6.75 (2H, m), 5.02 (2H, s), 5.08–4.91 (1H, m), 4.38–4.30 (2H, m), 4.11–3.99 (1H, m), 3.16–2.75 (6H, m), 2.21–2.05 (2H, m), 1.99–1.80 (1H, m), 1.80–1.61 (2H, m), 1.56–1.10 (5H, m), 1.36 (18H, s).

m.p.: 157–159° C. Mass(FAB(+)): m/z 769 (M+H)$^+$, 791 (M+Na)$^+$.

EXAMPLE 31

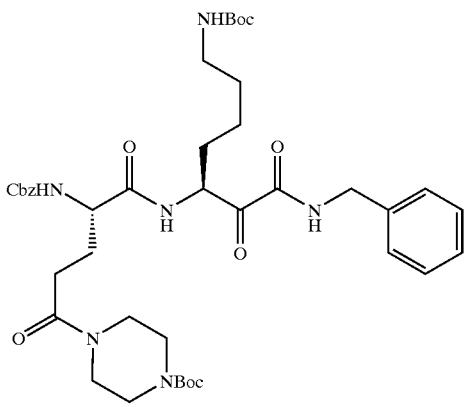

$^1$H-NMR (CDCl$_3$) δ: 9.23 (1H, t, J=6.2 Hz), 8.33–8.31 (1H, m), 7.44 (1H, d, J=8.0 Hz), 7.39–7.22 (10H, m), 6.80–6.66 (1H, m), 5.02 (2H, s), 5.05–4.90 (1H, m), 4.32 (2H, dq, J=7.1, 15.6 Hz), 4.13–3.96 (1H, m), 3.49–3.18 (8H, m), 2.95–2.75 (2H, m), 2.44–2.24 (2H, m), 1.92–1.77 (2H, m), 1.57–1.05 (6H, m), 1.40 (9H, s), 1.36 (9H, s).

m.p.: 60–65° C.

EXAMPLE 32

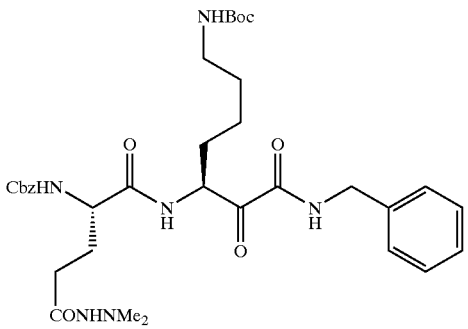

$^1$H-NMR (DMSO-d$_6$) δ: 12.20 (1H, brs), 9.25 (1H, m), 8.35 (1H, s), 7.70–7.20 (11H, m), 6.70 (1H, brs), 5.20–4.85 (3H, m), 4.35 (2H, m), 4.25 (1H, m), 3.20 (6H, s), 2.85 (2H, m), 2.25 (2H, m), 1.98–0.98 (8H, m), 1.35 (9H, s).
State: foamed material.

EXAMPLE 33

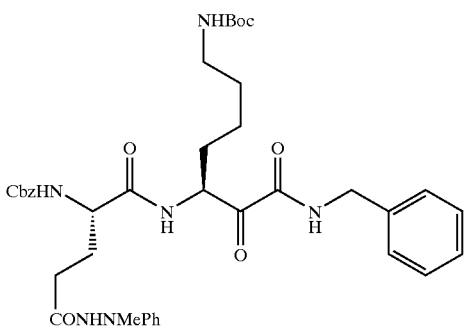

$^1$H-NMR (DMSO-d$_6$) δ: 9.88 (1H, s), 9.28–9.14 (1H, m), 8.31 (1H, d, J=6.8 Hz), 7.42 (1H, J=8.1 Hz), 7.37–7.15 (13H, m), 6.83–6.65 (3H, m), 5.04 & 5.02 (2H, s), 4.98–4.91 (1H, m), 4.34 (2H, dq, J=5.4, 11.5 Hz), 4.13–3.99 (1H, m), 3.06 (3H, s), 2.93–2.79 (2H, m), 2.37–2.14 (2H, m), 1.99–1.63 (3H, m), 1.56–1.24 (5H, m), 1.36 (9H, s).

m.p.: 147–150° C. Mass(FAB(+)): m/z 731 (M+H)$^+$, 753 (M+Na)$^+$.

EXAMPLE 34

A compound of the following formula was synthesized.

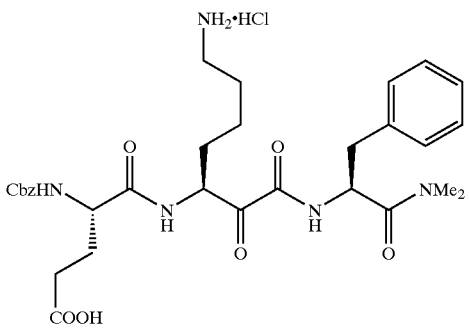

A 4N hydrochloric acid-ethyl acetate solution (2 ml) was added to 40 mg (0.052 mmols) of the compound obtained in Example 18, followed by stirring at room temperature for 2 hours. Anhydrous ether (20 ml) was added to the reaction mixture, and the resulting white precipitates were collected by filtration and washed with anhydrous ether, giving 23 mg of the above compound as a white powder (yield: 65%). The following are the properties of the compound.

$^1$H-NMR (DMSO-$d_6$) δ: 12.12 (1H, brs), 8.84 (1H, d, J=8.6 Hz), 8.25 (1H, t, J=6.0 Hz), 7.73 (3H, m), 7.47 (1H, d, J=7.6 Hz), 7.45–7.15 (10H, m), 5.00 (2H, ABq, J=12.5 Hz), 4.95–4.90 (2H, m), 4.05 (1H, dt, J=7.3, 7.6 Hz), 2.96 (2H, dq, J=3.6, 13.9 Hz), 2.92 (3H, s), 2.81 (3H, s), 2.65 (2H, m), 2.27 (2H, m), 1.91–1.64 (2H, m), 1.60–1.07 (6H, m).

m.p.: 130–132° C. Mass(FAB(+)): m/z 612 (M+H)$^+$.

In the following Examples 35 to 49, compounds shown therein were synthesized by following the procedure of Example 34 and using the corresponding compounds obtained in Examples 19 to 33.

EXAMPLE 35

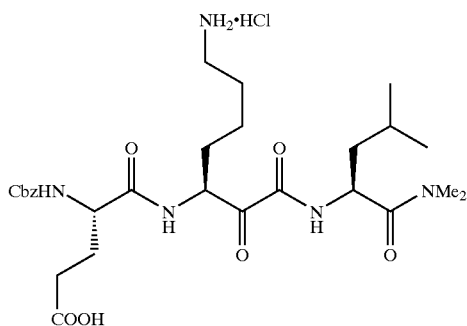

$^1$H-NMR (DMSO-$d_6$) δ: 12.14 (1H, brs), 8.67 (1H, d, J=8.3 Hz), 8.35 (1H, d, J=7.1 Hz), 7.82 (3H, m), 7.46 (1H, d, J=8.0 Hz), 7.37–7.30 (5H, m), 5.10–4.87 (3H, m), 4.72 (1H, dt, J=4.2, 10.1 Hz), 4.06 (1H, m), 3.02 (3H, s), 2.83 (3H, s), 2.80–2.65 (2H, m), 2.37–2.23 (2H, m), 2.00–1.13 (11H, m), 0.89 (3H, d, J=6.6 Hz), 0.87 (3H, d, J=6.6 Hz).

Mass(FAB(+)): m/z 578 (M+H)$^+$.
State: foamed material.

EXAMPLE 36

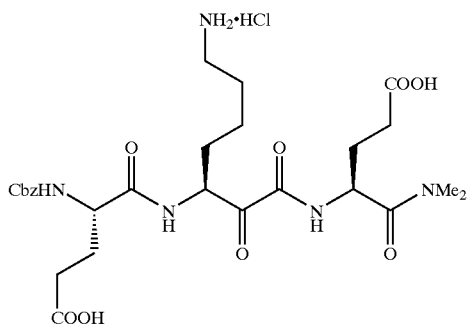

$^1$H-NMR (DMSO-$d_6$) δ: 12.14 (2H, brs), 8.65 (1H, d, J=8.1 Hz), 8.37 (1H, d, J=6.8 Hz), 7.82 (3H, m), 7.45 (1H, d, J=7.6 Hz), 7.42–7.28 (5H, m), 5.01 (2H, ABq, J=12.7 Hz), 4.97 (1H, m), 4.75 (1H, m), 4.06 (1H, m), 3.05 (3H, s), 2.84 (3H, s), 2.77 (2H, m), 2.37–2.21 (4H, m), 1.98–1.34 (10H, m).

Mass(FAB(+)): m/z 594 (M+H)$^+$.
State: foamed material

EXAMPLE 37

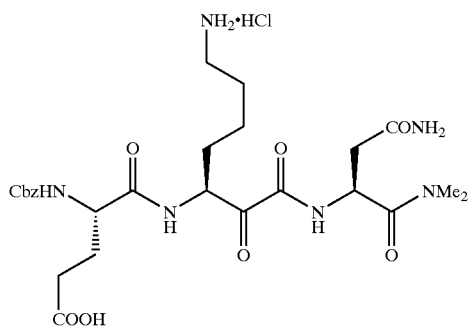

$^1$H-NMR (DMSO-$d_6$) δ: 8.92 & 8.88 (1H, d, J=8.5, 7.8 Hz), 8.36 (1H, d, J=7.1 Hz), 7.91 (3H, m), 7.49–7.25 (7H, m), 6.88 (1H, brs), 5.12–4.90 (3H, m), 4.15–3.93 (2H, m), 3.02 (3H, s), 2.81 (3H, s), 2.80–2.19 (6H, m), 2.07–1.16 (8H, m).

Mass(FAB(+)): m/z 579 (M+H)$^+$.
State: foamed material

EXAMPLE 38

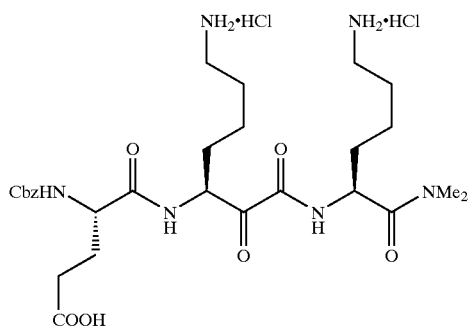

$^1$H-NMR (DMSO-$d_6$) δ: 9.11 (1H, d, J=6.8 Hz), 8.76 (1H, d, J=7.8 Hz), 7.98 (6H, m), 7.47–7.28 (7H, m), 5.05–4.90 (3H, m), 4.66 (1H, m), 3.52 (3H, s), 2.86 (3H, s), 2.74 (4H, m), 2.50–2.20 (2H, m), 2.05–1.20 (14H, m).

Mass(FAB(+)): m/z 593 (M+H)$^+$.
State: foamed material

EXAMPLE 39

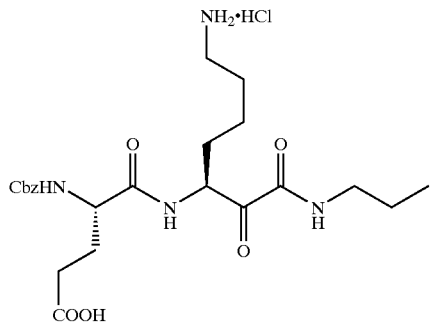

$^1$H-NMR (DMSO-$d_6$) δ: 12.11 (1H, brs), 8.73 (1H, t, J=6.10 Hz), 8.34 (1H, d, J=6.6 Hz), 7.74 (3H, m), 7.45 (1H, d, J=7.8 Hz), 7.39–7.29 (5H, m), 5.01 (2H, ABq, J=12.4 Hz), 5.00–4.92 (1H, m), 4.09–4.04 (1H, m), 3.12–3.03 (2H, m), 2.83–2.71 (2H, m), 2.29 (2H, t, J=8.0 Hz), 1.93–1.30 (10H, m), 0.82 (3H, t, J=7.4 Hz).

m.p.: 173–175° C. (decomp.). Mass(FAB(+)): m/z 479 (M+H)⁺.

EXAMPLE 40

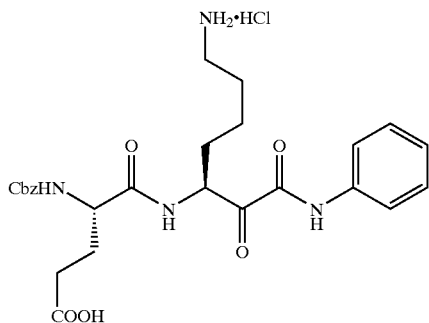

¹H-NMR (DMSO-d₆) δ: 12.13 (1H, s), 10.62 (1H, s), 8.49–8.47 (1H, m), 7.79 (2H, d, J=8.4 Hz), 7.76–7.62 (3H, m), 7.48 (1H, d, J=7.6 Hz), 7.40–7.28 (7H, m), 7.14 (1H, t, J=7.4 Hz), 5.09–5.00 (1H, m), 5.01 (2H, ABq, J=12.9 Hz), 4.13–4.05 (1H, m), 2.85–2.74 (2H, m), 2.31 (2H, t, J=8.3 Hz), 1.95–1.29 (8H, m).

m.p.: 172–175° C. (decomp.).

EXAMPLE 41

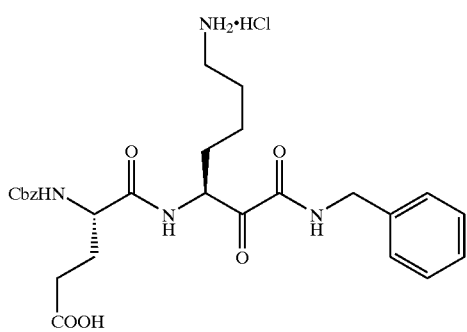

¹H-NMR (DMSO-d₆) δ: 12.12 (1H, brs), 9.30 (1H, t, J=6.4 Hz), 8.39 (1H, d, J=6.6 Hz), 7.76 (3H, m), 7.46 (1H, d, J=7.8 Hz), 7.39–7.22 (10H, m), 5.01 (2H, ABq, J=12.4 Hz), 4.97–4.95 (1H, m), 4.32 (2H, dq, J=6.6, 14.9 Hz), 4.07 (1H, dq, J=5.8, 8.5 Hz), 2.76–2.67 (2H, m), 2.30 (2H, t, J=8.1 Hz), 1.94–1.22 (8H, m).

m.p.: 172–174° C. Mass(FAB(+)): m/z 527 (M+H)⁺.

EXAMPLE 42

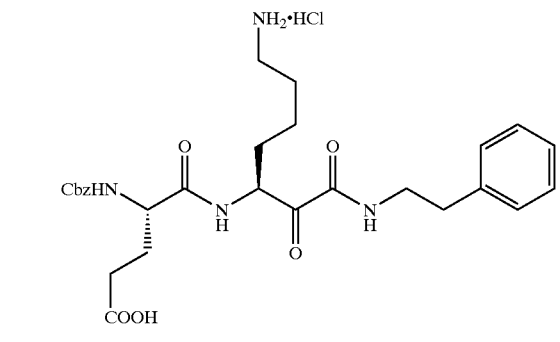

¹H-NMR (DMSO-d₆) δ: 12.12 (1H, brs), 8.82 (1H, t, J=5.8 Hz), 8.33 (1H, d, J=6.6 Hz), 7.86–7.69 (3H, m), 7.45 (1H, d, J=8.0 Hz), 7.41–7.19 (10H, m), 5.01 (2H, ABq, J=12.7 Hz), 4.97–4.91 (1H, m), 4.07 (1H, dt, J=8.0, 5.6 Hz), 2.53–2.50 (2H, m), 2.80–2.76 (4H, m), 2.29 (2H, t, J=7.9 Hz), 1.94–1.18 (8H, m).

m.p.: 148–151° C. (decomp.). Mass(FAB(+)): m/z 541 (M+H)⁺.

EXAMPLE 43

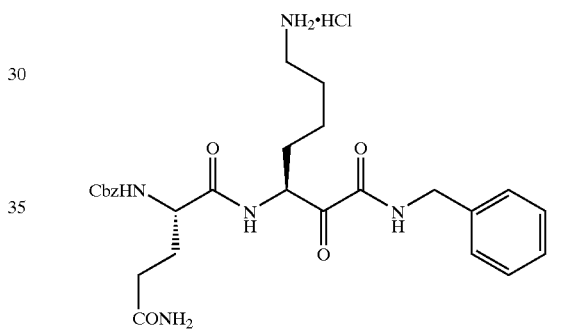

¹H-NMR (DMSO-d₆) δ: 9.28 (1H, t, J=6.5 Hz), 8.38 (1H, d, J=6.8 Hz), 7.93–7.74 (3H, brs), 7.42 (1H, d, J=8.0 Hz), 7.37–7.24 (11H, m), 6.77 (1H, brs), 5.01 (2H, s), 5.03–4.98 (1H, m), 4.32 (2H, dq, J=6.4, 14.9 Hz), 4.13–4.00 (1H, m), 2.84–2.62 (2H, m), 2.30–1.19 (10H, m).

m.p.: 183–185° C. (decomp.). Mass(FAB(+)): m/z 526 (M+H)⁺.

EXAMPLE 44

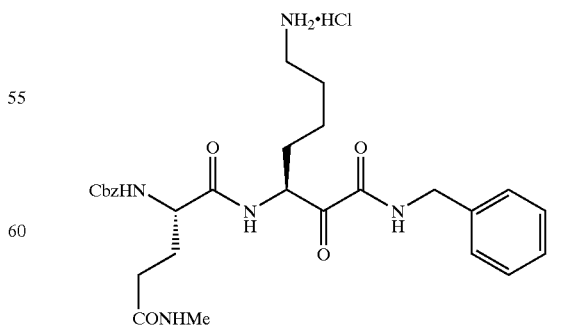

¹H-NMR (DMSO-d₆) δ: 9.28 (1H, t, J=6.4 Hz), 8.38 (1H, d, J=6.8 Hz), 7.88 (3H, brs), 7.74 (1H, q, J=4.5 Hz), 7.43

(1H, d, J=7.8 Hz), 7.37–7.22 (10H, m), 5.04–4.99 (1H, m), 5.02 (2H, s), 4.32 (2H, dq, J=6.4, 15.0 Hz), 4.04 (1H, dt, J=5.1, 8.6 Hz), 2.82–2.72 (2H, m), 2.55 (3H, d, J=4.6 Hz), 2.25–2.05 (2H, m), 2.01–1.13 (8H, m).

m.p.: 157–159° C. (decomp.). Mass(FAB(+)): m/z 540 (M+H)$^+$.

EXAMPLE 45

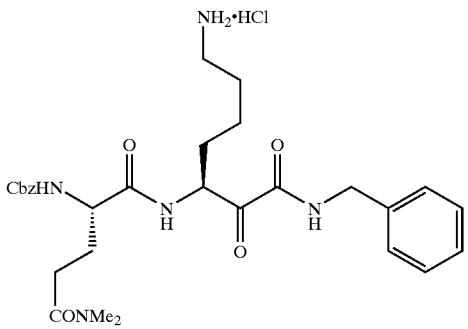

$^1$H-NMR (DMSO-d$_6$) δ: 9.28 (1H, t, J=6.3 Hz), 8.43 (1H, d, J=6.6 Hz), 7.87 (3H, m), 7.47 (1H, q, J=7.8 Hz), 7.46–7.22 (10H, m), 5.04–4.97 (1H, m), 5.01 (2H, ABq, J=12.7 Hz), 4.32 (2H, dq, J=6.0, 14.5 Hz), 4.10–4.06 (1H, m), 2.93 (3H, s), 2.80 (3H, s), 2.83–2.71 (2H, m), 2.35 (2H, t, J=7.8 Hz), 1.91–1.24 (8H, m).

m.p.: 137–140° C. (decomp.). Mass(FAB(+)): m/z 554 (M+H)$^+$.

EXAMPLE 46

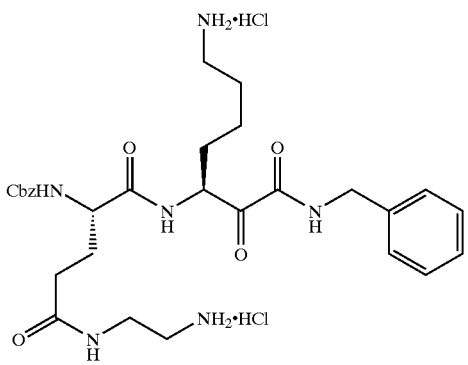

$^1$H-NMR (DMSO-d$_6$) δ: 9.28 (1H, t, J=6.2 Hz), 8.42 (1H, d, J=6.6 Hz), 8.11 (1H, t, J=5.0 Hz), 8.00 (3H, brs), 7.90 (3H, brs), 7.45 (1H, d, J=8.3 Hz), 7.36–7.24 (10H, m), 5.02 (2H, s), 5.10–4.94 (1H, m), 4.32 (2H, dq, J=6.6, 15.4 Hz), 4.11–4.03 (1H, m), 3.41–3.27 (2H, m), 2.89–2.79 (2H, m), 2.79–2.60 (2H, m), 2.30–2.11 (2H, m), 1.99–1.84 (1H, m), 1.84–1.75 (1H, m), 1.66–1.20 (6H, m).

m.p.: 180–185° C. (decomp.). Mass(FAB(+)): m/z 569 (M+H)$^+$.

EXAMPLE 47

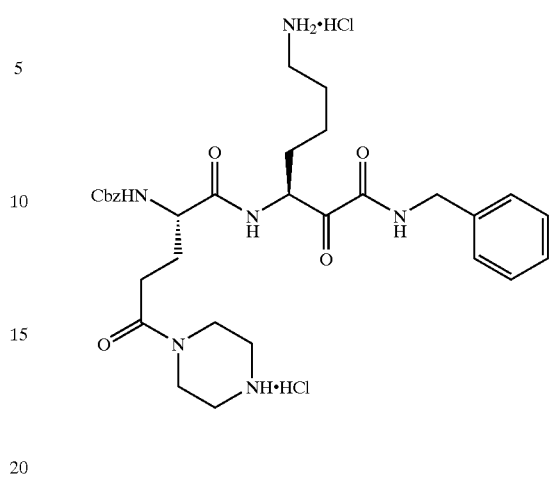

$^1$H-NMR (DMSO-d$_6$) δ: 9.39 (2H, brs), 9.28 (1H, t, J=6.5 Hz), 8.46 (1H, d, J=6.8 Hz), 7.91 (3H, m), 7.46 (1H, d, J=8.0 Hz), 7.36–7.19 (10H, m), 5.02 (2H, s), 5.09–4.91 (1H, m), 4.33 (2H, dq, J=6.8, 15.4 Hz), 4.08–4.02 (1H, m), 3.76–3.55 (4H, m), 3.17–2.95 (4H, m), 2.83–2.75 (2H, m), 2.45–2.31 (2H, m), 1.94–1.05 (8H, m).

m.p.: 168–171° C. (decomp.). Mass(FAB(+)): m/z 595 (M+H)$^+$.

EXAMPLE 48

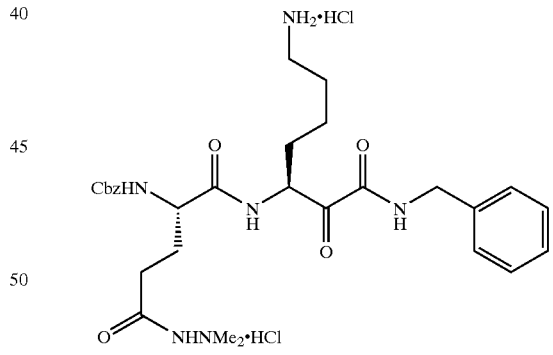

$^1$H-NMR (DMSO-d$_6$) δ: 9.28 (1H, t, J=6.3 Hz), 8.43 (1H, d, J=6.6 Hz), 7.87 (3H, brs), 7.47 (1H, q, J=7.8 Hz), 7.46–7.22 (10H, m), 5.04–4.97 (1H, m), 5.01 (2H, ABq, J=12.7 Hz), 4.32 (2H, m), 4.10–4.06 (1H, m), 2.93 (3H, s), 2.80 (3H, s), 2.83–2.71 (2H, m), 2.35 (2H, t, J=7.8 Hz), 1.91–1.24 (8H, m).

m.p.:131–133° C. Mass(FAB(+)): m/z 569 (M+H)$^+$.

EXAMPLE 49

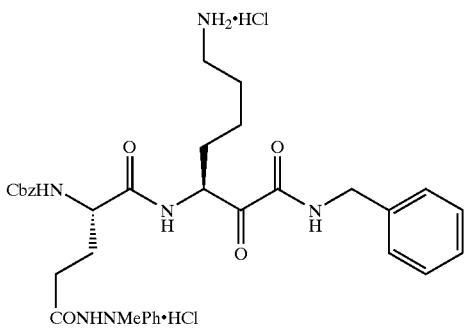

$^1$H-NMR (DMSO-$d_6$) δ: 9.90 (1H, s), 9.28 (1H, t, J=5.6 Hz), 8.37–8.32 (1H, m), 7.80–7.62 (3H, m), 7.45 (1H, d, J=7.8 Hz), 7.40–7.10 (13H, m), 6.73 (2H, d, J=7.1 Hz), 5.03 (2H, s), 5.03–4.98 (1H, m), 4.32 (2H, dq, J=6.8, 15.2 Hz), 4.13–4.00 (1H, m), 3.06 (3H, s), 2.83–2.67 (2H, m), 2.36–2.17 (2H, m), 2.03–1.67 (3H, m), 1.63–1.25 (6H, m).
m.p.: 153–155° C. Mass(FAB(+)): m/z 631 (M+H)$^+$.

| Formulation Example 1 Oral ointment | |
| --- | --- |
| Compound 1 of the invention obtained in Example 1 | 1.0 |
| White petrolatum | 10 |
| Sodium polyacrylate | 3.0 |
| Liquid paraffin | Balance |
| Total | 100.0 (wt. %) |

An oral ointment was prepared by a conventional process using the above ingredients.

| Formulation Example 2 Dentifrice | |
| --- | --- |
| Calcium secondary phosphate | 42 |
| Glycerin | 19 |
| Carrageenan | 0.9 |
| Sodium lauryl sulfate | 1.2 |
| Saccharin | 1.0 |
| Compound 12 of the invention obtained in Example 12 | 1.0 |
| Butyl paraoxybenzoate | 0.005 |
| Flavor | 1.0 |
| Water | Balance |
| Total | 100.0 (wt. %) |

A dentifrice was prepared by a conventional process using the above ingredients.

| Formulation Example 3 Troche | |
| --- | --- |
| Gum arabic | 6.0 |
| Glucose | 72.0 |
| Lactose | 19.0 |
| Compound 34 of the invention obtained in Example 34 | 1.5 |
| Sodium monofluorate | 0.7 |
| Flavor | 1.0 |
| Water | Balance |
| Total | 100.0 (wt. %) |

Troches were prepared by a conventional process using the above ingredients.

| Formulation Example 4 Chewing gum | |
| --- | --- |
| Polyvinyl acetate | 20.0 |
| Polyisobutylene | 3.0 |
| Calcium carbonate | 2.0 |
| Sorbitol | 55.0 |
| Mannitol | 15.0 |
| Compound 39 of the invention obtained in Example 39 | 4.0 |
| Flavor | 1.0 |
| Total | 100.0 (wt. %) |

Chewing gum was prepared by a conventional process using the above ingredients.

| Formulation Example 5 Gargle | |
| --- | --- |
| Ethanol | 20.0 |
| Polyoxyethylene (60) hydrogenated castor oil | 3.0 |
| Polyethylene glycol | 2.0 |
| Glycerin | 10.0 |
| Sodium saccharin | 0.02 |
| Compound 43 of the invention obtained in Example 43 | 0.5 |
| Flavor | 0.2 |
| Water | Balance |
| Total | 100.0 (wt. %) |

A gargle was prepared by a conventional process using the above ingredients.

| Formulation Example 6 Mouthwash | |
| --- | --- |
| Ethanol | 30.0 |
| Polyoxyethylene (20) sorbitan laurate | 1.0 |
| Polyoxyethylene (40) hydrogenated castor oil | 0.5 |
| Sodium hydroxide | 0.05 |
| Sodium saccharin | 0.05 |
| Compound 46 of the invention obtained in Example 46 | 0.5 |
| Flavor | 0.5 |
| Water | Balance |
| Total | 100.0 (wt. %) |

A mouthwash was prepared by a conventional process using the above ingredients.

TEST EXAMPLE 1
Measurement of Inhibitory Activity Against KGP

The inhibitory activity against Lys-gingipain (KGP) was measured by the method described in Journal Biochemistry, Vol. 123, 305–312 (1998), using Z-His-Glu-Lys-MCA as a substrate. Specifically, the measurement was carried out in the following manner: 100 μl of 50 mM L-cystein, 200 μl of a 0.1 M sodium phosphate buffer solution (pH 7.5), 20 μl of 12.3 nM KGP solution containing 0.05% "Brij35" (a tradename of Aldrich, polyoxyethylene(23) lauryl ether), 80 μl of distilled water and 100 μl of a dimethyl sulfoxide solution of a compound according to the invention were mixed together, and preincubated at 37° C. for 5 minutes. Thereafter, 500 μl of a 0.1% dimethyl sulfoxide solution containing 20 μM Z-His-Glu-Lys-MCA was added, followed by incubation at 40° C. for 10 minutes. Then, an acetic acid buffer solution (pH 5.0) containing 10 mM iodoacetamide was added to stop the enzyme reaction, and the fluorescence intensity (F) at 460 nm excited at 380 nm was measured. As a control, 100 μl of a dimethyl sulfoxide solution that did not contain the compound according to the invention was used in place of the solution of the compound, and the fluorescence intensity ($F_0$) was measured in a manner similar to the above. The enzyme inhibitory activity (%) was calculated by the following equation.

Enzyme inhibitory activity (%)=[1−(F/$F_0$)]×100

The inhibitory activity against Arg-gingipain (hereinafter referred to as "RGP") was measured for comparison in a manner similar to the above, by the process described in Journal Biological Chemistry, Vol. 269, 21371–21378 (1994) using Z-Phe-Arg-MCA as a substrate.

Table 1 shows the inhibitory activities of the compound of the invention against KGP and RGP.

TABLE 1

| Compound (Ex. No.) | Concentration (mol/l) | Enzyme inhibitory activity (%) KGP | RGP |
|---|---|---|---|
| 34 | $10^{-6}$ | 99.7 | 5.7 |
|    | $10^{-9}$ | 40.6 | — |
| 35 | $10^{-6}$ | 99.9 | 3.7 |
|    | $10^{-9}$ | 50.6 | — |
| 36 | $10^{-6}$ | 98.6 | 0.0 |
|    | $10^{-9}$ | 38.4 | — |
| 37 | $10^{-6}$ | 99.9 | 8.5 |
|    | $10^{-9}$ | 59.6 | — |
| 39 | $10^{-6}$ | 99.6 | 0.0 |
|    | $10^{-9}$ | 71.9 | — |
| 40 | $10^{-6}$ | 99.6 | 0.0 |
|    | $10^{-9}$ | 71.3 | — |
| 41 | $10^{-6}$ | 99.7 | 4.0 |
|    | $10^{-9}$ | 81.8 | — |
| 42 | $10^{-6}$ | 98.0 | 7.7 |
|    | $10^{-9}$ | 67.0 | — |
| 43 | $10^{-6}$ | 100.0 | 9.0 |
|    | $10^{-9}$ | 93.8 | — |
| 44 | $10^{-6}$ | 100.0 | 1.9 |
|    | $10^{-9}$ | 97.3 | — |
| 45 | $10^{-6}$ | 100.0 | 0.0 |
|    | $10^{-9}$ | 93.7 | — |
| 46 | $10^{-6}$ | 99.9 | 0.5 |
|    | $10^{-9}$ | 99.9 | — |
| 47 | $10^{-6}$ | 100.0 | 6.4 |
|    | $10^{-9}$ | 98.5 | — |
| 48 | $10^{-6}$ | 100.0 | 4.1 |
|    | $10^{-9}$ | 98.2 | — |
| 49 | $10^{-6}$ | 100.0 | 0.0 |
|    | $10^{-9}$ | 99.0 | — |

Table 1 reveals that the compound of the invention specifically inhibits, with a high activity, the enzymatic activity of KGP.

The compound of the invention is useful as, for example, a prophylactic or therapeutic agent for periodontal disease, because of its high and specific activity to inhibit the activity of Lys-gingipain (KGP) produced by *Porphyromonas gingibvalis*, which is a Gram-negative anaerobic bacterium.

What is claimed is:

1. A peptide derivative of formula (I)

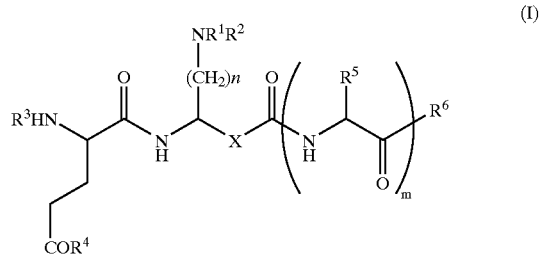

wherein X is —CHOH— or —CO—; $R^1$ and $R^2$ may be the same or different and are hydrogen or substituted oxycarbonyl; $R^3$ is substituted oxycarbonyl; $R^4$ is hydroxyl, lower alkoxy, optionally substituted piperazinyl, or —$NR^7R^8$ (wherein $R^7$ and $R^8$ may be the same or different and are hydrogen, optionally substituted lower alkyl, or amino optionally substituted with lower alkyl(s) or aryl(s)); $R^5$ is a R-group side chain of an α-amino acid optionally protected by a protective group; $R^6$ is hydroxyl, lower alkoxy, or —$NR^9R^{10}$ (wherein $R^9$ and $R^{10}$ may be the same or different and are hydrogen, lower alkyl, aryl or aralkyl); m is 0 or 1; and n is an integer of 2 to 6; or a pharmaceutically acceptable salt thereof.

2. The peptide derivative according to claim 1 wherein n is 4; or a pharmaceutically acceptable salt thereof.

3. The peptide derivative according to claim 1 wherein X is —CO—; or a pharmaceutically acceptable salt thereof.

4. The peptide derivative according to claim 1 wherein $R^1$ and $R^2$ may be the same or different and are hydrogen or lower alkyloxycarbonyl and $R^3$ is optionally substituted aralkyloxycarbonyl; or a pharmaceutically acceptable salt thereof.

5. The peptide derivative according to claim 4 wherein $R^4$ is hydroxyl, lower alkoxy, piperazinyl optionally having lower alkyl as a substituent, or —$NR^7R^8$ (wherein $R^7$ and $R^8$ may be the same or different and are hydrogen, lower alkyl optionally having amino or lower alkoxycarbonylamino as a substituent, or amino optionally substituted with lower alkyl(s) or phenyl(s)); $R^6$ is hydroxyl, lower alkoxy or —$NR^9R^{10}$ (wherein $R^9$ and $R^{10}$ may be the same or different and are hydrogen, lower alkyl, phenyl, benzyl or phenethyl); and n is 4; or a pharmaceutically acceptable salt thereof.

6. The peptide derivative according to claim 5 wherein m is 0 and $R^6$ is hydroxyl or —$NR^9R^{10}$ (wherein $R^9$ and $R^{10}$ may be the same or different and are lower alkyl or phenethyl, or one of $R^9$ and $R^{10}$ is hydrogen and the other is phenethyl); or a pharmaceutically acceptable salt thereof.

7. The peptide derivative according to claim 5 wherein m is 1, $R^5$ is isobutyl, carbamoylmethyl optionally protected by a protective group, 2-carboxyethyl optionally protected by a protective group, 4-aminobutyl optionally protected by a protective group, or benzyl, and $R^6$ is —$NR^9R^{10}$ (wherein $R^9$ and $R^{10}$ may be the same or different and are lower alkyl); or a pharmaceutically acceptable salt thereof.

8. The peptide derivative according to claim 1 wherein X is —CO—, $R^1$ and $R^2$ are hydrogen, $R^3$ is benzyloxycarbonyl, $R^4$ is hydroxyl, $R^5$ is isobutyl, carbamoylmethyl, 2-carboxyethyl, 4-aminobutyl or benzyl, $R^6$ is —$NR^9R^{10}$ (wherein $R^9$ and $R^{10}$ are methyl), m is 1, and n is 4; or a pharmaceutically acceptable salt thereof.

9. The peptide derivative according to claim 1 wherein X is —CO—, $R^1$ and $R^2$ are hydrogen, $R^3$ is benzyloxycarbonyl, $R^4$ is hydroxyl, amino, methylamino, dimethylamino, (2-aminoethyl)amino, piperazinyl, 1,1-dimethylhydrazino or 1-methyl-1-phenylhydrazino, $R^6$ is n-propylamino, phenylamino, benzylamino or phenethylamino, m is 0, and n is 4; or a pharmaceutically acceptable salt thereof.

10. A Lys-gingipain inhibitor comprising the peptide derivative of formula (I) of claim 1 or a pharmaceutically acceptable salt thereof as an active ingredient.

11. A pharmaceutical preparation for periodontal disease comprising the peptide derivative of formula (I) of claim 1 or a pharmaceutically acceptable salt thereof as an active ingredient.

12. A composition for use in the oral cavity comprising the peptide derivative of formula (I) of claim 1 or a pharmaceutically acceptable salt thereof and a pharmaceutically acceptable carrier.

* * * * *